US008530508B2

(12) United States Patent
Gewirtz et al.

(10) Patent No.: US 8,530,508 B2
(45) Date of Patent: Sep. 10, 2013

(54) THROMBOPOIETIN RECEPTOR AGONIST (TPORA) KILLS ACUTE HUMAN MYELOID LEUKEMIA CELLS

(75) Inventors: Alan Gewirtz, Philadelphia, PA (US); Anna Kalota, Philadelphia, PA (US); Connie L. Erickson-Miller, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 66 days.

(21) Appl. No.: 12/682,114

(22) PCT Filed: Oct. 8, 2008

(86) PCT No.: PCT/US2008/079205
§ 371 (c)(1),
(2), (4) Date: Jul. 30, 2010

(87) PCT Pub. No.: WO2009/048953
PCT Pub. Date: Apr. 16, 2009

(65) Prior Publication Data
US 2010/0298398 A1 Nov. 25, 2010

Related U.S. Application Data

(60) Provisional application No. 60/998,126, filed on Oct. 9, 2007.

(51) Int. Cl.
*A01N 43/56* (2006.01)
*A61K 31/415* (2006.01)

(52) U.S. Cl.
USPC .......................................... 514/404

(58) Field of Classification Search
None
See application file for complete search history.

(56) References Cited

U.S. PATENT DOCUMENTS

| 5,342,947 | A | 8/1994 | Lackey et al. |
| 5,491,237 | A | 2/1996 | Fang et al. |
| 5,559,235 | A | 9/1996 | Luzzio et al. |
| 5,681,835 | A | 10/1997 | Willson |
| 5,877,219 | A | 3/1999 | Willson |
| 6,063,923 | A | 5/2000 | Fang et al. |
| 6,100,273 | A | 8/2000 | Besterman et al. |
| 6,207,716 | B1 | 3/2001 | Willson |
| 6,268,391 | B1 | 7/2001 | Dickerson et al. |
| 6,737,062 | B2 | 5/2004 | Nicolette |
| 6,887,890 | B2 | 5/2005 | Fujiwara et al. |
| 7,026,334 | B1 | 4/2006 | Takemoto et al. |
| 7,160,870 | B2 | 1/2007 | Duffy et al. |
| 7,314,887 | B2 | 1/2008 | Chen et al. |
| 7,547,719 | B2 | 6/2009 | Moore |
| 2003/0171306 | A1* | 9/2003 | Davis et al. ............... 514/27 |
| 2003/0195231 | A1 | 10/2003 | Takemoto et al. |
| 2004/0053946 | A1 | 3/2004 | Lackey et al. |
| 2004/0077697 | A1 | 4/2004 | Koshio et al. |
| 2004/0192654 | A1* | 9/2004 | Gourdeau et al. ........... 514/85 |
| 2005/0153977 | A1 | 7/2005 | Sugasawa et al. |
| 2006/0116417 | A1 | 6/2006 | Chen et al. |
| 2007/0105824 | A1 | 5/2007 | Erickson-Miller et al. |
| 2007/0129539 | A1 | 6/2007 | Zhi et al. |
| 2010/0075928 | A1* | 3/2010 | Erickson-Miller ........... 514/150 |
| 2011/0129550 | A1* | 6/2011 | Erickson-Miller ........... 424/649 |
| 2011/0160130 | A1* | 6/2011 | Erickson-Miller ........... 514/7.8 |

FOREIGN PATENT DOCUMENTS

| EP | 1 104 674 | 8/2001 |
| WO | WO99/22733 | 5/1999 |
| WO | WO 99/11262 | 11/1999 |
| WO | WO 01/89457 | 11/2001 |
| WO | WO 02/59099 | 1/2002 |
| WO | WO 02/59100 | 1/2002 |
| WO | WO03/098992 | 12/2003 |
| WO | WO2004/096154 | 11/2004 |
| WO | WO2007/044982 | 4/2007 |
| WO | WO2007/062078 | 5/2007 |
| WO | WO2007/106564 | 9/2007 |
| WO | WO2008/073864 | 6/2008 |
| WO | WO2009/151862 | 12/2009 |
| WO | WO2010/045310 | 4/2010 |

OTHER PUBLICATIONS

Abraham, R. T., *Current Opinion in Immunology*, 8(3):412-8 (1996), 6,268,391.
Ashby, M.N., *Current Op. in Lipidology*, 9(2):99-102 (1998).
Bolen, et al., *Annual Review of Immunology*, 15:371-404 (1997).
Brekken, et al., *Cancer Research*, 60:5117-5124 (2000).
Brodt, et al., *Biochemical Pharm.*, 60:1101-1107 (2000).
Bruns, et al., *Cancer Research*, 60:2926-2935 (2000).
Canman, et al., *Oncogene*, 17(25):3301-3308 (1998).
Chen, et al., *Blood*, 86:4054-4062 (1995).
Chen, et al., *Cancer Research*, 58:1965-1971 (1988).
Cwirla, *Science*, 276:1696 (1997).
Einzig, et al., *Proc. Am. Soc. Clin. Oncol.*, 20:46 (2001).
Ezumi, et al., *FEBS Letters*, 374:48-52 (1995).
Forastire, et al., *Sem. Oncol.*, 20:56 (1990).
Gauduchon, et al., *Clinical Cancer Research*, 11:2345-2354 (2005).
Green, et al., *Cancer Treat. Rev.*, 26(4):269-286 (2000).
Greene, "Protective Groups in Organic Synthesis", 1981, Table of Contents.
Hasegawa, *Int. J. Immunopharm.*, 18:103-112 (1996).
Holmes, et al., *J. Nat. Cancer Inst.*, 83:1797 (1991).
Jackson, S. P., *International Journal of Biochemistry and Cell Biology*, 29(7):935-8 (1997).
Kojima, et al., *Thrombosis and Haemostasis*, 74:1541-1545 (1995).
Kath, John C., *Exp. Opin. Ther. Patents*, 10(6):803-818 (2000).
Kearns, et al., *Seminars in Oncology*, 3(6):16-23 (1995).
Kingston, et al., *Studies in Organic Chemistry*, 26:219-235 (1986).
Kitada, et al., *Antisense Res. Dev.*, 4:71-79 (1994).
Komatsu, *Blood*, 87:4552 (1996).

(Continued)

*Primary Examiner* — Brandon Fetterolf
*Assistant Examiner* — Anna Pagonakis
(74) *Attorney, Agent, or Firm* — Wayne J. Dustman; Edward R. Gimmi

(57) ABSTRACT

The present invention provides methods of inhibiting human myeloid leukemia cell growth and proliferation by administering a thrombopoietin receptor agonist (TpoRA), a derivative, or variant thereof, to an individual with AML.

3 Claims, 18 Drawing Sheets

(56) References Cited

OTHER PUBLICATIONS

Kumar, *J. Biol. Chem.*, 256:10435-10441 (1981).
Kuter, et al., *Seminars in Hematology*, 37:41-49 (2000).
Lackey, K., et al., *Bioorganic and Medicinal Chemistry Letters*, 10:223-226 (2000).
Lamb, et al., *Nucleic Acids Research*, 23:3283-3289 (1995).
Laurenz, et al., *Comp. Biochem. & Phys., Part A Physiology*, 116:369-377 (1997).
Lofts, et al., *New Molecular Targets for Cancer Chem.*, 1994.
Markman, et al., *Yale Journal of Biology and Medicine*, 64:583 (1991).
Martinez-Iacaci, L., et al., *Int. J. Cancer*, 88(1):44-52 (2000).
Massague, et al., *Cancer Surveys*, 27:41-64 (1996).
McCabe, et al., *Cancer Research*, 66:8109-8115 (2006).
McDonald, et al., Am. J. of Pediatric Hematology/Oncology, 1992, vol. 14, No. 1, pp. 8-21.
McGuire, et al., *Ann. Intern. Med.*, 111:273 (1989).
Metcalf, et al., Nature, Jun. 16, 1994, vol. 369, pp. 519-520.
Philip, et al., *Cancer Treatment and Research*, 78:3-27 (1995).
Reilly, et al., *Cancer Research*, 60:3569-3576 (2000).
Rosania, et al., *Exp. Opin. Ther. Patents*, 10(2):215-230 (2000).
Scharovsky, et al., *Journal of Biomedical Sciences*, 7(4):292-8 (2000).
Schiff, et al., *Proc. Natl. Acad. Sci.*, 77:1561-1565 (1980).
Schiff, et al., *Nature*, 277:665-667 (1979).
Schreiber, et al., *Science*, 232:1250-1253 (1986).
Seidel, *Proc. Natl. Acad. Sci. USA*, 92:3041-3045 (1995).
Shawyer, et al., *DDT*, 2(2):Feb. 1997.
Shiotsu, et al., *Exp. Hemat.*, 26:1195-1201 (1998).
Sinh, et al., *Journal of Hematotherapy and Stem Cell Res.*, 8(5):465-80 (1999).
Smithgall, T. E., *Journal of Pharmacological and Toxicological Methods*, 34(3):125-32 (1995).
Stern, *Breast Cancer Research*, 2:176-183 (2000).
Vigon, *Proc. Natl. Acad. Sci. USA*, 89:5640-5644 (1992).
Wani, et al., *J. Am. Chem. Soc.*, 93:2325 (1971).
Water, et al., *J. Clin. Oncol.*, 18:1812-1823 (2000).
Woo, et al., *Nature*, 368:750 (1994).
Yamamoto, et al., *Journal of Biochemistry*, 126(5):799-803 (1999).
Yen, et al., *Oncogene*, 19:3460-3469 (2000).
Zhelev, et al., *Cancer Chemotherapy Pharmacology*, 53:267-275 (2004).
Zhong, et al., *Cancer Res.*, 60(6):1541-1545 (2000).

\* cited by examiner

Figure 7 (CONTINUED)

1-solute carrier family 1 (neutral amino acid transporter
2-E2F transcription factor 4, p107/p130-binding
3-chromosome 4 open reading frame 9
4-Fc Fragment of IgG, low affinity IIC
5-forkhead box K2
6-translocase of inner mitochondrial membrane 44
7-engulfment and cell motility 2
8-PR domain containing 2, w/ ZNF domain
9-Solute carrier family 2 (facil. Glucose transport.)
10-BMP2 inducible kinase
11-chromosome 15 open reading frame 44 ///
12-zinc finger protein 410
13-EPH receptor A2
14-chaperonin containing TCP1, subunit 6A (zeta 1)
15-KIAA0586
16-SPFH domain family member 2
17-Carboxypeptidase M
18-SH3 domain and and tetratricopeptide repeats 2
19-neurotrophic tyrosine kinase receptor type 3
20-unknown protein LOC51035
21-Tyrosine 3-monooxygenase/tryptophan 5-monox
22-phospholipid scramblase 3
23-hypothetical protein DKFZp76112123
24-LDLR-FUT fusion protein
25-villin 2 (ezin)
26-KIAA0888 protein
27-vacuolar protein sorting 53 (S. cerevisiae)
28-bone morphogenetic protein recept, type IA
29-syntaphilin
30-mitogen activated protein kinase 13
31-chromosome 3 open reading frame 28
32-peroxinedoxin 2
33-EF-hand calcium binding protein 2
34-methylthioadenosine phosphorylase
35--
36-formin homology 2 domain containing 3
37-NGFI-A binding protein 1 (EGR1 binding protein 1)
38-SUMO1/sentrin specific peptidase 6
39-adenosine deaminase, RNA_specific, B1
40-SW1/SNF related matrix associated actin depend.
41-obscurin-like 1
42-secretogranin V (7B2 protein)
43-leucine-rich repeats and immunoglobulin like domain
44-chromosome 17 open reading frame 86
45-amyloid beta (A4) precursor protein binding
46-chromosome 4 open reading frame 8
47-angiogenic factor with G patch and FHA domains 1
48-carboxypeptidase A3 (mast cell)
49-proteasome (prosome, macropain) subunit. Beta
50-coatomer protein complex subunit alpha
51-transmembrane protein 118
52-allograft inflammatory factor 1
53-Jumanji AT rich interactive domain 1A (RBBP2-like)
54-c-myc binding protein
55-neutrophil cytosolic factor 4 40kDa
56-alpha thalassemia/mental retardation syndrome X
57-chromosome 17 open reading frame 75
58-natural killer tumor recognition sequence
59-synaptonemal complex protein 1
60-oxysterol binding protein-like 1A
61-Hypothetical protein LOC339524
62-FK506 binding protein 8, 38kDa

Figure 8A (CONTINUED)

1-BCL2/adenovirus E1B 19kDa interacting protein
2-programmed cell death 10
3-Tax1 (human T cell leukemia virus type I binding
4-SH3 domain GRB2 like enophilin B1
5-calreticulin
6-transglutaminase 2 (C polypeptide, protein glutami...)
7-CD27-binding Siva protein
8-Translocase of outer mitochondrail membrane 40
9-baculoviral IAP repeat containing 5 (survivin)
10-BCL2-associated X protein
11-testis enhanced gene transcript (BAX inhibitor 1)
12-EF hand domain (C terminal) containing 1
13-CD27 binding Siva protein
14-ATPase Ca++ transporting plasma membrane
15-CASP8 and FADD like apoptosis regulator
16-BCL2/adenovirus E1B 19kDa interacting protein 1
17-non-metastatic cells 6, protein expressed in (nucl...)
18-high mobility group box 1
19-testis enhanced gene transcript (BAX inhibitor 1)
20-SAP30 binding protein
21-v-raf murine sarcoma viral oncogene homolog B1
22-CASP8 associated protein 2
23-protein phosphatase 1 (formerly 2A)
24-beclin 1 (coiled coil, myosin like BCL2 interacting...)
25-fission 1 (mitochondrial outer membrane) homolog
26-nucleoporin 62kDa
27-rabaptin, RAB GTPase binding effector protein 1
28-nucleophosmin (nulceolar phophoprotein B23)
29-voltage dependent anion channel 1
30-TRIAD3 protein
31-SCAN domain containing 1
32-tumor necrosis factor (ligand) superfamily
33-DNA fragmentation factor 40kDa beta polypeptide
34-tumor necrosis factor (ligand) superfamily
35-CD40 molecule, TNF receptor superfamily
36-P21/Cdc42/Rac1-activated kinase 1 (STE20)
37-Islet amyloid polypeptide
38-Programmed cell death 6
39-ATG12 autophagy related 12 homolog
40-death effector domain containing
41-tumor protein p53 (Li-Fraumeni syndrome)
42-zinc finger and BTB domain containing 16
43-programmed cell death 4 (neoplastic transformation)
44-phosphoprotein enriched in astrocytes 15
45-baculoviral IAP repeat containing 5 survivin
46-Fas TNF receptor superfamily member 6
47-D site of albumin promoter Albumin D box
48-GULP engulfment adaptor PTB domain
49-CD40 molecule TNF receptor superfamily
50-NCK associated protein 1
51-presenilin 1 (Alzheimer disease 3)
52-Fragile X mental retardation autosomal homolog 1
53-death effector domain containing
54-ubiquitination factor E4B (UFD2 homolog yeast)
55-Translocase of outer mitochondrial membrane 40
56-CASP8 and FADD-like apoptosis regulator

Figure 8B (CONTINUED)

1-suppressor of cytokine signaling 3)
2-protein phosphatase 1 regulatory inhibitor
3-Cell division cycle 2-like 2 (PITSLRE proteins)
4-TNF receptor associated factor 4
5-myeloid cell leukemia sequence 1 BCL2-related
6-pim-1 oncogene /// pim-1 oncogene
7-myeloid cell leukemia sequence 1 BCL2-related
8-extra spindle poles like 1 (S. cerevisiae)
9-suppressor of cytokine signaling 2
10-caspase 9, apoptosis related cysteine peptidase
11-heat shock 70 kDa protein 1A
12-promyelocytic leukemia
13-BCLA associated athanagene 3
14-TNFRSF1A associated via death domain
15-retinoic acid receptor alpha
16-cell division cycle 2-like 1 (PITSLRE protein)
17-engulfment and cell motility 2
18-ATP binding cassette sub family A (ABC1)
19-protein phosphatase 1 regulatory inhibitor subunit
20-caspase recruitment domain family, member 4
21-valosin containing protein
22-protein phosphatase 1F (PP2C domain containing)
23-v-abl Abelson murine leukemia viral oncogene
24-promyelocytic leukemia
25-suppressor of cytokine signaling 2
26-cytokine induced apoptosis inhibitor 1
27-death associated protein 6
28-cell division cycle 2-like 1 (PITSLRE proteins)
29-cathepsin B
30-transforming growth factor beta regulator 4
31-heat shock 70kDa protein 1B
32-TNF receptor associated factor 3
33-ras homolog gene family member 12
34-inhibitor of kappa light polypeptide gene enhancer
35-lymphotoxin beta receptor (TNFR superfamily)
36-ras homolog gene family member 8
37-mal T cell differentiation protein
38-protein phosphatase 1F (PP2C domain containing)

Figure 9B (CONTINUED)

1-early growth response 3
2-inhibitor of DNA binding 1
3-early growth response 4
4-FOS like antigen 1
5-B cell CLL lymphoma 3
6-early growth response 1
7-early growth response 2
8-v-fos FBJ murine osteosarcoma viral oncogene
9-FBJ murine osteosarcoma viral oncogene
10-basic helix loop helix domain containing class B,2
11-v-mal musculoaponeurotic fibrosarcoma onc.
12-FOS-like antigen 2
13-SNF1-like kinase
14-jun B proto oncogene
15-early growth response 1
16-v-mal musculoaponeurotic fibrosarcoma onc.
17-nuclear receptor subfamily 2 group F memb.2
18-vitamin D (1,25 dihydroxyvitamin D3) receptor
19-nuclear receptor subfamily 2 group F memb.2
20-splicing factor 1
21-retinoic acid receptor alpha
22-zinc finger protein 324
23-distal-less homeobox 2
24-nuclear receptor subfamily 2 group F memb.2
25-SERTA domain containing 3
26-serum response factor (c-fos serum resp. elem.)
27-tribbles homolog 3 (Drosophila)
28-KIAA0194
29-zinc finger protein 202
30-nuclear transcription factor Y, alpha
31-nuclear receptor subfamily 2 group F memb.2
32-thyroid hormone receptor alpha
33-E1A binding protein p400

THROMBOPOIETIN RECEPTOR AGONIST (TPORA) KILLS ACUTE HUMAN MYELOID LEUKEMIA CELLS

This application is a 371 of International Application No. PCT/US2008/079205, filed Oct. 8, 2008, which claims the benefit of U.S. Provisional Application No. 60/998,126, filed Oct. 9, 2007, which are incorporated herein in their entirety.

BACKGROUND OF THE INVENTION

About 11,920 new cases of acute myelogenous leukemia (AML; also known as acute myelocytic leukemia, acute myeloid leukemia, acute myeloblastic leukemia, acute granulocytic leukemia or acute nonlymphocytic leukemia) were diagnosed in the United States in 2005 (Surveillance, Epidemiology and End Results [SEER] Program, 2005). The most common acute leukemia affecting adults, AML can occur at any age, but adults age 65 and older are more likely to develop the disease than younger people. In addition, AML accounts for about 15 to 20 percent of childhood acute leukemia cases.

The malignant cell in AML is the myeloblast. In normal hematopoiesis, the myeloblast is an immature precursor of myeloid white blood cells. However, in AML, a single myeloblast accumulates genetic changes which "freeze" the cell in its immature state and prevents differentiation. Such a mutation alone does not cause leukemia; however, when "differentiation arrest" is combined with other mutations which disrupt genes controlling proliferation, the result is the uncontrolled growth of an immature clone of cells (leukemic blasts) which fail to function as normal blood cells and also block production of normal marrow cells. This leads to a deficiency of red cells (anemia), platelets (thrombocytopenia), and normal white cells, especially neutrophils (neutropenia) in the blood, leading to the clinical presentation of AML.

Nearly all patients with AML require treatment as soon after diagnosis as possible. In most patients, intensive chemotherapy (induction therapy), during which at least two different chemotherapeutic agents are administered, is required to achieve remission.

Remission is achieved when blood cell counts gradually approach normal and leukemia cells cannot be identified in blood or marrow. However, in remission, residual leukemic cells are still present but inactive; they do not interfere with normal blood cell development but do have the potential to re-grow and cause a relapse of the leukemia. For this reason, additional chemotherapy with or without autologous stem cell infusion or allogeneic stem cell transplantation usually is advised.

Residual leukemic cells that cannot be detected in the blood or by marrow examination remain in the body during remission. Optimal treatment of AML, therefore, usually requires additional intensive therapy after remission has been achieved (consolidation therapy). Even after the intensive chemotherapy of consolidation therapy, some patients have residual leukemic cells in their marrow (refractory leukemia) and still other patients suffer "relapse" after achieving remission.

One of the greatest difficulties to overcome when treating a patient with AML is that the leukemia cells of some patients are insensitive to chemotherapy drugs. This can lead to a failure of treatment to induce or sustain remission.

There are three known mechanisms of drug resistance in the leukemia cell that protect it from the effects of chemotherapy. First, specific genes encode proteins that evolved to protect the primitive cells from toxins (e.g. P-glycoprotein (multi-drug resistant protein), lung resistance protein, and breast cancer resistance protein). These proteins, and others, may decrease the effectiveness of chemotherapy in acute leukemia cells. Second, chemotherapy takes advantages of apoptosis gene pathways by inducing accentuated and accelerated programmed cell death. In some leukemias, however, these genes are either down-regulated or even blocked, literally blocking cell death as a result of chemotherapy. Third, specific gene families may be active in chemotherapy-resistant cells that result in relapse of the patient's leukemia. To date, no new successful clinical approaches have been found that block one or another of these pathways.

Although the proportion of patients with AML who enter remission, stay in remission for years, or are actually cured, has increased over the past 30 years, AML remains one of the most difficult blood cancers to cure. Because of this difficulty, new therapies for treating AML are essential. There is therefore, a longstanding, urgent need in the art for new methods of treating this devastating disease. The present invention fulfills this need.

SUMMARY OF THE INVENTION

One embodiment of the invention comprises a method of treating a human diagnosed with acute myelogenous leukemia, the method comprising administering a composition comprising a thrombopoietic receptor agonist (TpoRA), a derivative, or variant thereof, to the human, further wherein the composition inhibits leukemia cell growth and proliferation in the human. In one aspect, the composition is administered to the human before, during or after the administration of a chemotherapeutic agent. On another aspect, a TpoRA, a derivative or variant thereof is administered to the human as a pharmaceutical composition comprising the TroRA, derivative or variant thereof and a pharmaceutical carrier. In another aspect, the pharmaceutical composition is administered parentally to the human. In still another aspect, the thrombopoietin receptor agonist is Compound A.

Another embodiment of the invention comprises a method of treating a human diagnosed with myelodysplastic syndrome, the method comprising administering a composition comprising a thrombopoietic receptor agonist (TpoRA), a derivative, or variant thereof, to the human, further wherein the composition inhibits leukemia cell growth and proliferation in the human. In one aspect, the composition is administered to the human before, during or after the administration of a chemotherapeutic agent. In another aspect, a TpoRA, a derivative or variant thereof is administered to the human as a pharmaceutical composition comprising the TroRA, derivative or variant thereof and a pharmaceutical carrier. In another aspect, the pharmaceutical composition is administered parentally to said human. In still another aspect, the thrombopoietin receptor agonist is Compound A.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A through FIG. 1C, is a series of charts depicting the megakaryocyte colony forming assay. FIG. 1A is an image depicting human CD34+ cells grown in fibrin clots in presence of thrombopoietin (TPO). FIG. 1B is an image depicting human CD34+ cells grown in fibrin clots in presence of Compound A. FIG. 1C is a graph depicting of the number of colonies formed from CD34+ cells after stimulation with TPO or Compound A.

FIG. 2A through FIG. 2C, is a series of charts depicting growth curves representing proliferation study of human primary leukemia cells exposed to TPO or Compound A. FIG. 2A is a pair of charts depicting the effect of TPO, Compound A (SB), Control (CTRL) and DMSO on primary cells obtained from two patients with acute myeloid leukemia (AML). The total number of cells is shown on the Y-axis and various time points (Day 0, 3, and 4) are shown on the X-axis. FIG. 2B is a pair of charts depicting the effects of TPO, Compound A (SB), Control (CTRL) and DMSO on primary cells obtained from two patients with acute lymphoid leukemia (ALL). The total number of cells is shown on the Y-axis and various time points (Day 0, 1, 3, and 5) are shown on the X-axis. FIG. 2C is a pair of charts depicting the effects of TPO, Compound A (SB), Control (CTRL) and DMSO on primary cells obtained from two patients with chronic myeloid leukemia (CML). The total number of cells is shown on the Y-axis and various time points (Day 0, 3, and 6) are shown on the X-axis.

FIG. 3A through FIG. 3F, is a series of charts depicting the effect of control, DMSO, 2.8 µM TPO, 5 µM Compound A (SB), 2.5 µM Compound A (SB), and 1 µM Compound (SB) on growth of primary leukemia cells obtained from patients with AML. FIG. 3A is a chart depicting effects of 1, 2.5, and 5 µM of Compound A (SB) and 2.8 µM TPO on cell growth of primary leukemia cells obtained from patient AML 857. FIG. 3B is a chart depicting effects of 1, 2.5, and 5 µM of Compound A (SB) and 2.8 µM TPO on cell growth of primary leukemia cells obtained from patient AML 794. FIG. 3C is a chart depicting effects of 1, 2.5, and 5 µM of Compound A (SB) and 2.8 µM TPO on cell growth of primary leukemia cells obtained from patient AML 342. FIG. 3D is a chart depicting effects of 1, 2.5, and 5 µM of Compound A (SB) and 2.8 µM TPO on cell growth of primary leukemia cells obtained from patient AML 332. FIG. 3E is a chart depicting effects of 1, 2.5, and 5 µM of Compound A (SB) as well as 2.8 µM TPO on cell growth of primary leukemia cells obtained from patient AML 774. FIG. 3F is a chart depicting effects of 1, 2.5, and 5 µM of Compound A (SB) and 2.8 µM TPO on cell growth of primary leukemia cells obtained from patient AML 759. Cells were counted on days 3, 5 and 8 in all experiments.

FIG. 4A and FIG. 4B, is a series of images depicting Western blot analysis of phosphorylation of kinases involved in TPO signaling. FIG. 4A is an image depicting a Western blot UT&-TPO cells. FIG. 4B in an image depicting Western blots of human progenitor cells CD34+. Compound A is designated as SB.

FIG. 5A through FIG. 5F, is a series of charts depicting the results of proliferation assays. FIG. 5A is a chart depicting results of a proliferation assay carried out on primary leukemia cells obtained from AML patient 857. FIG. 5B is a chart depicting results of a proliferation assay carried out on primary leukemia cells obtained from AML patient 794. FIG. 5C is a chart depicting results of a proliferation assay carried out on primary leukemia cells obtained from AML patient 342. FIG. 5D is a chart depicting results of a proliferation assay carried out on primary leukemia cells obtained from AML patient 332. FIG. 5E is a chart depicting results of a proliferation assay carried out on primary leukemia cells obtained from AML patient 774. FIG. 5F is a chart depicting results of a proliferation assay carried out on primary leukemia cells obtained from AML patient 759. Compound A is designated as SB.

FIG. 8, comprising FIG. 8A is an image depicting a heat map illustrating genes involved in apoptotic pathway in N2C-TPO cells which are upregulated by stimulation with TPO vs Compound A. FIG. 8B is an image depicting a heat map illustrating genes involved in apoptotic pathway in N2C-TPO cells that are down-regulated by stimulation with TPO vs Compound A. Changes in gene expression in cells stimulated with Compound A indicated by a lighter color.

FIG. 9, comprising FIG. 9A is an image depicting a heat map illustrating transcription factors that are upregulated in N2C-TPO cells stimulated with TPO vs Compound A. FIG. 9B is an image depicting a heat map illustrating transcription factors that are downregulated in N2C-TPO cells stimulated with TPO vs Compound A. Changes in gene expression in cells stimulated with Compound A indicated by a lighter color.

DETAILED DESCRIPTION OF THE INVENTION

Figure 1:
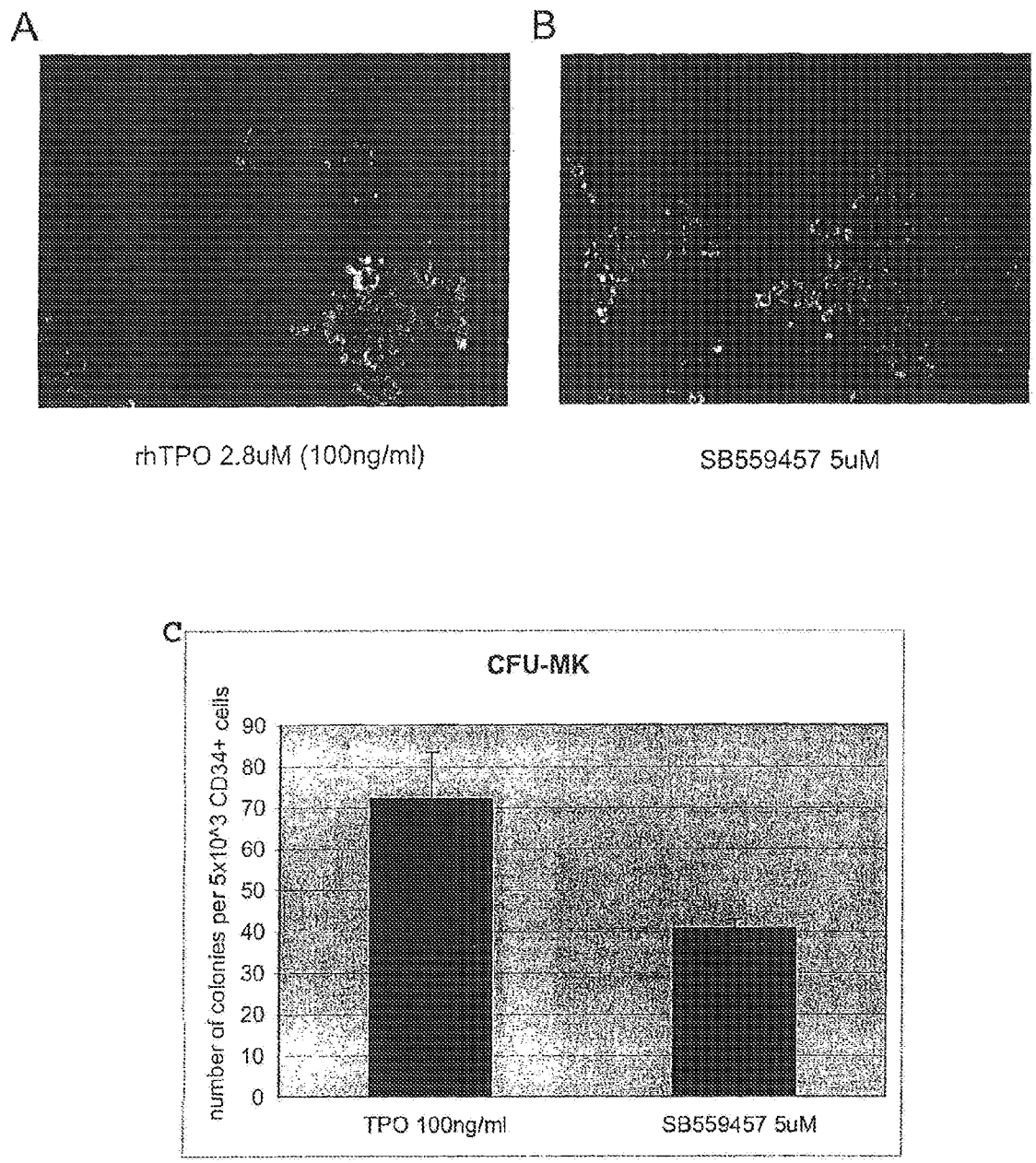
FIG. 1, comprising

The present invention provides methods of inhibiting human myeloid leukemia cell growth and proliferation by administering a thrombopoietin receptor agonist (TpoRA), a derivative, or variant thereof, to an individual with AML. In one embodiment, a TpoRA, a derivative, or variant thereof is administered to an individual with AML. In another embodiment of the invention, TpoRA, a derivative, or variant thereof is administered to an individual with AML as part of a chemotherapeutic regimen.

DEFINITIONS

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e. to at least one) of the grammatical object of the article. By way of example, "an element" means one element or more than one element.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "agonist" and "agonistic" when used herein refer to or describe a molecule which is capable of, directly or indirectly, substantially inducing, promoting or enhancing biological activity or receptor activation.

The term "chemotherapy" as used herein, refers to course of treatment wherein a chemotherapeutic agent is administered to an individual diagnosed with a cancer. A chemotherapeutic agent includes agents such as drugs which can advantageously be administered to an individual with cancer, to treat said cancer. The chemotherapeutic agent often comprises an apoptosis inducing agent which induces apoptosis in cells, e.g., tumor cells. Cells, including cancer cells, can be induced to undergo programmed cell death, also known as apoptosis. Apoptosis is characterized by the selective programmed destruction of cells into relatively small fragments with DNA becoming highly fragmented (i.e. the resulting fragments typically have no more than about 200 bases). During apoptosis, cell shrinkage and internucleosomal DNA cleavage occurs, which results in the fragmentation of the DNA.

The term "derivative" is used to define a compound that has been derived from another, specifically a compound comprising any modification of Compound A of the present invention that retains the bioactivity of Compound A as described in the present invention.

The term "DNA" as used herein is defined as deoxyribonucleic acid.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The phrase "leucopenia" as used herein, refers to a decrease below normal in the concentration of blood leukocytes (white cells) in a mammal.

The phrase "mutation" as used herein, refers to an alteration in a gene that results from a change to a part of the stretch of DNA that represents a gene.

A "germ cell mutation" is present in the egg or the sperm and can be transmitted from parent(s) to offspring.

A "somatic cell mutation" occurs in a specific tissue cell and can result in the growth of the specific tissue cell into a tumor. Most cancers start after a somatic mutation. In leukemia, lymphoma or myeloma, a primitive marrow or lymph node cell undergoes a somatic mutation(s) that leads to the formation of a tumor. In these cases, the tumors are usually widely distributed when detected; they involve the marrow of many bones or involve lymph nodes in several sites, usually.

The phrase "oncogene" as used herein, refers to a mutated gene that is the cause of a cancer. Several subtypes of acute myelogenous leukemia, acute lymphocytic leukemia, lymphoma, and nearly all cases of chronic myelogenous leukemia have a consistent mutated gene (oncogene).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The phrase "Polymerase Chain Reaction (PCR)" as used herein, refers to a technique to expand trace amounts of DNA or RNA so that the specific type of the DNA or RNA can be studied or determined. This technique has become useful in detecting a very low concentration of residual leukemia or lymphoma cells, too few to be seen using a microscope. The technique can detect the presence of one leukemic cell among five hundred thousand to one million nonleukemic cells. PCR requires a specific DNA (or RNA) abnormality or marker, like an oncogene, in the leukemic or lymphomatous cells for its use to identify residual abnormal cells.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means.

The phrase "refractory (disease)" as used herein, refers to disease that does not go into remission or improve substantially after initial treatment with standard therapy for the disease.

The phrase "relapse (recurrence)" as used herein, refers to a return of the disease after it has been in remission following treatment.

The phrase "remission" as used herein, refers to a disappearance of evidence of a disease, usually as a result of treatment. The terms "complete" or "partial" are used to modify the term "remission." Complete remission means all evidence of the disease is gone. Partial remission means the disease is markedly improved by treatment, but residual evidence of the disease is present. Long-term benefit usually requires a complete remission, especially in acute leukemia or progressive lymphomas.

The phrase "resistance to treatment" as used herein, refers to the ability of cells to live and divide despite their exposure to a chemical that ordinarily kills cells or inhibits their growth. Refractory leukemia is the circumstance in which a proportion of malignant cells resist the damaging effects of a drug or drugs. Cells have several ways to develop drug resistance.

The term "therapeutic" as used herein means a treatment and/or prophylaxis. A therapeutic effect is obtained by suppression, remission, or eradication of a disease state associated with liver disease.

The phrase "thrombocytopenia" as used herein, refers to a decrease below normal in the concentration of the blood platelets in a mammal.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. The term variant can also refers to a modification made to a molecule which does not alter its function.

DESCRIPTION

The present invention provides methods using a thrombopoietin receptor agonist to inhibit human myeloid leukemia cell growth and proliferation. The method of the present invention is useful in the treatment of cellular proliferative and/or differentiative disorders particularly those related to acute myeloid leukemia.

Thrombopoietin Receptor Agonists in the Present Invention

The invention includes the use of a thrombopoietic receptor agonist (TpoRA) to inhibit the growth and proliferation of AML cells. The terms "thrombopoietin receptor agonist" or "TPO receptor agonist" (TpoRA) are used interchangeably herein and include any pharmaceutical compound, small molecule, peptide or nucleic acid that possesses the property of binding to the thrombopoietin receptor, mpl, and having a biological property of a mpl agonist. In the present invention, the biological property of the TPO receptor agonist is the inhibition of the growth and proliferation of AML cells.

A preferred TpoRA useful in the method of the invention is 3'-{N'-[1-(3,4-dimethylphenyl)-3-methyl-5-oxo-1,5-dihydropyrazol-4-ylidene]hydrazine}-5'-fluoro-2'-hydroxybiphenyl-3-carboxylic acid, hereafter known as Compound A. Compound A is a compound which is disclosed (as Example 13) and claimed, along with pharmaceutically acceptable salts, hydrates, solvates and esters thereof, as being useful as an agonist of the TPO receptor, particularly in enhancing platelet production and particularly in the treatment of thrombocytopenia, in International Application No. PCT/US01/16863 (International Publication Number WO 01/89457; United States Publication Number US2004/0019190 A1), the disclosure of which is hereby incorporated by reference, and whose structure is as follows:

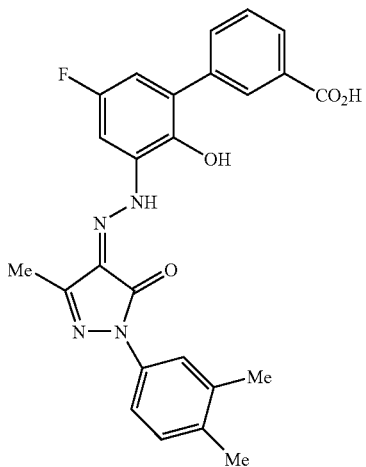 [SMILES: CC1=NN(c2ccc(C)c(C)c2)C(=O)/C1=N\Nc1cc(F)cc(-c2cccc(C(=O)O)c2)c1O]

Methods of Treatment

In one embodiment of the methods of the present invention, a TpoRA, a derivative or a variant thereof, is administered to an individual diagnosed with AML. In one aspect of the invention, a TpoRA, derivative, or variant thereof is administered to an individual with AML as part of a chemotherapeutic regimen to augment the efficacy of a chemotherapeutic agent.

In another embodiment of the methods of the present invention, a TpoRA, a derivative or a variant thereof, is administered to an individual diagnosed with myelodysplastic syndrome. In one aspect of the invention, a TpoRA, derivative, or variant thereof is administered to an individual with myelodysplastic syndrome as part of a chemotherapeutic regimen to augment the efficacy of a chemotherapeutic agent.

By "augment the efficacy of a chemotherapeutic agent" it is meant that administering a TpoRA, derivative, or variant thereof will bring about a beneficial clinical outcome including, but not limited to, increasing the survival of the individual, reducing clinical signs of AML or myelodysplastic syndrome in the individual, or by permitting a reduction in the dose of the chemotherapeutic agent or the frequency of administration of the chemotherapeutic agent, or both, thereby reducing the undesirable side effects associated with the toxicity of the chemotherapeutic agents and making the chemotherapeutic regimen more tolerable. A TpoRA, derivative, or variant thereof may be administered to an individual either before the administration of the chemotherapeutic agent, during the administration of the chemotherapeutic agent or after the administration of the chemotherapeutic agent, or some combination thereof, deemed to be effective for treatment of the individual. Establishing the optimal schedule for administering a TpoRA, a derivative, or variant thereof as part of a chemotherapeutic regimen is well within the skill of the art.

In another aspect of the invention, a TpoRA, a derivative, or variant thereof is administered to the individual prior to the administration of chemotherapy. Without wishing to be bound by any theory, it will be appreciated by one skilled in the art that administering a TpoRA to the individual prior to the commencement of chemotherapy would target leukemia cells resistant to chemotherapy and would augment the efficacy of a chemotherapeutic agent. In addition, all leukemia cells that express a TPO receptor are targets of a TpoRA, a derivative or variant thereof. It will be apparent to one skilled in the art that providing a TpoRA, derivative or variant thereof to an individual before commencing chemotherapy would make leukemia cells more susceptible to chemotherapeutic agents, thereby making treatment more efficacious.

In yet another aspect of the invention, a TpoRA, a derivative, or variant thereof is administered to the individual after the individual has completed a course of chemotherapy. Without wishing to be bound by any theory, it will be appreciated by one skilled in the art that residual, undetected circulating leukemia cells increase the risk of relapse in AML patients after completion of chemotherapy. Administering a TpoRA, a derivative, or variant thereof to the individual who has completed a course of chemotherapy targets residual leukemia cells while they are still inactive and reduces the risk of disease recurrence.

In still another aspect of the invention, a TpoRA, a derivative, or variant thereof is administered to the individual in lieu of chemotherapy as the sole method of treating AML. It will be appreciated by one skilled in the art that in a number of individuals diagnosed with AML, the leukemia cells are refractory to chemotherapy. Treating these individuals with a TpoRA, a derivative, or variant thereof is an alternative therapy that bypasses the mechanisms that allow the leukemia cells to evade chemotherapeutic agents.

In still another aspect of the invention, a TpoRA, a derivative, or variant thereof is administered to the individual in lieu of chemotherapy as the sole method of treating AML.

The compositions and methods of the present invention can be used in combination with other treatment regimens, including virostatic and virotoxic agents, antibiotic agents, antifungal agents, anti-inflammatory agents, pain-reduction therapies, as well as combination therapies, and the like.

The invention can also be used in combination with other treatment modalities, such as chemotherapy, cryotherapy, hyperthermia, radiation therapy, and the like.

Therapies and Pharmaceutical Preparations

A TpoRA, a derivative, or a variant thereof can be administered to the individual using any suitable route known in the art, including for example, intravenous treatment protocols. Administration can be either by rapid, direct injection or over a period of time as by slow infusion. Slow release formulation may also be used. Furthermore, a TpoRA, a derivative, or variant thereof can be stably linked to a polymer such as polyethylene glycol to confer desirable properties such as solubility, stability, extended half-life and other pharmaceutically advantageous properties to the TpoRA (see, e.g. Burnham, 1994, AM. J. Hosp. Pharm. 51:210-8).

Phosphatase inhibitors and activators, and kinase inhibitors and activators, can also be linked or conjugated to TpoRA to confer desirable properties such as solubility, stability, extended half-life and other pharmaceutically advantageous properties to the TpoRA.

The invention encompasses the use of pharmaceutical compositions to practice the methods of the invention, the compositions comprising an appropriate therapeutic compound and a pharmaceutically-acceptable carrier.

As used herein, the term "pharmaceutically-acceptable carrier" means a chemical composition with which a therapeutic compound may be combined and which, following the combination, can be used to administer the appropriate therapeutic compound to a mammal.

The pharmaceutical compositions useful for practicing the invention may be administered to deliver a dose of between 1 ng/kg/day and 100 mg/kg/day. The precise dosage administered will vary depending upon any number of factors, including but not limited to, the type of animal and type of disease state being treated, the age of the animal and the route of administration. It is well within the skill of the art to establish the optimal dosage of a TpoRA, a derivative or variant thereof required for maximal clinical benefit.

Pharmaceutical compositions that are useful in the methods of the invention may be administered systemically in intravenous formulations. In addition to the appropriate therapeutic compound, such pharmaceutical compositions may contain pharmaceutically-acceptable carriers and other ingredients known to enhance and facilitate drug administration.

The invention encompasses the preparation and use of pharmaceutical compositions comprising a compound useful for treatment of AML disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Pharmaceutical compositions that are useful in the methods of the invention may be prepared, packaged, or sold in formulations suitable for parenteral, intravenous or another route of administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, infrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in micro-crystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The compound may be administered to the individual as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the individual, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Compounds

Compound A was obtained from Glaxo SmithKline Pharmaceuticals (Collegeville, Pa.). The compound was dissolved in 100% DMSO to prepare a 10 mM stock solution and then diluted in IMDM (Iscoves Modified Dulbecco's Medium, Invitrogen; Carlsbad, Calif.) to obtain a 1 mM working solution. Full length recombinant human thrombopoietin (rhTPO) was obtained form R&D Systems (Minneapolis, Minn.) and dissolved in IMDM medium to final concentration 5 ng/ml.

Cell Culture

N2C-TPO cells were derived by culture of a megakaryblastic cell line in rhTpo for 10 weeks and provided by Glaxo SmithKline Pharmaceuticals (Collegeville, Pa.). N2C-TPO cells were cultured in RPMI (Invitrogen, Carlsbad, Calif.) medium supplemented with 10% Animal Serum Complex—Fetalplex (Gemini Bio-Products, West Sacramento, Calif.), 0.5% Penicillin/Streptomycin (Invitrogen; Carlsbad, Calif.) and 20 ng/ml rhTPO.

Mo7e cells were cultured in DMEM (Dulbecco's Modified Eagle Medium; Invitrogen, Carlsbad, Calif.) supplemented with 10% Fetalplex, 0.5% Penicillin/Streptomycin, and GM-CSF 10 ng/ml (R&D Systems, Minneapolis, Minn.). Cells from both cell lines were starved for 24 hours before each experiment.

Human primary leukemia cells were obtained from Stem Cell and Leukemia Core at the University of Pennsylvania. Cells were cultured in EGM-2 (Endothelial Cell Medium-2, Cambrex; East Rutherford, N.J.). All cells were cultured in humidified incubator at 37° C. and 5% $CO_2$.

Megakaryocyte Colony Forming Assay

Normal human progenitor cells were plated in fibrinogen clots at a density of 5000 CD34+ cells per ml. Fibrinogen clots were prepared as follow: cells were re-suspended in IMDM medium supplemented with sodium bicarbonate (3 mg/ml); 3-mercapto-1-2propanediol (0.002%); transferring (300 µg/ml); $CaCl_2$ (37 µg/ml); fatty acid free, deionized BSA (10%); insulin (20 µg/ml); cholesterol (5.6 µg/ml) cytokines: IL-3 (10 ng/ml), SCF (10 ng/ml) and rhTPO (100 ng/ml equal 2.8 µM) or Compound A (5 µM). Then clotting mix containing fibrinogen (0.2%) and thrombin (0.2 u/ml). Cells were plated on 35 mm culture dishes and cultured in humidified incubator at 37° C. and 5% $CO_2$. After 10 days, colonies were fixed and stained for megakaryocyte marker CD41a with fluorescently labeled antibody. Megakaryocyte colonies were counted using inverted fluorescent microscope.

Western Blot Analysis of Kinases Phosphorylation

Controls and cells stimulated with rhTPO or Compound A were washed twice in PBS, then pelleted. The pellet was dissolved in triple-lysis buffer comprised of 50 mM TRIS, 150 mM NaCl, 0.02% sodium azide, 0.1% sodium dodecyl sulphate (SDS) and 1% Igepal (Sigma, St. Louis, Mo.), and then incubated for 30 min on ice with vortexing every 10 min. The lysate was then spun at maximum speed in a microcentrifuge at 4° C. for 10 min. The extracted cell supernatant was used for Western-blot analysis.

Protein concentration was determined by a Bradford protein assay (Bio-Rad, Hercules, Calif.). A total of 150 µg protein extract was resolved on a 10% polyacrylamide gel (150V, 60 min.) then transferred to a poly vinylidene fluoride (PVDF) membrane (25V, 60 min). Condensed milk (5%) was used as a blocking solution. The membrane was incubated overnight at 4° C. with primary antibody at a 1:1000 dilution. After incubation, the membrane was washed three times in TBS-T buffer and probed with secondary HRP-conjugated antibody (Amersham Biosciences; Piscataway, N.J.) at dilution 1:1000 for 2 hour at room temperature. All antibodies were purchased from Cell Signaling Technology (Danvers, Mass.).

Microarray Analysis

N2C-TPO cells ($1 \times 10^6$ cells per 1 ml of RPMI medium supplemented with 10% FBS) were stimulated with 2.8 uM TPO or 5 uM Compound A for 30 minutes, 1 and 3 hours. Then cells were washed twice in PBS and used to isolate RNA using Qiagen's RNaesy kit (Valencia, Calif.). Each condition was done in triplicate. RNA was submitted to Penn Microarray Facility (University of Pennsylvania; Philadelphia, Pa.). Analysis was performed using Affymetrix GeneChip U133A vs 2. Statistical data analysis was performed in Penn Bioinformatics Core (University of Pennsylvania; Philadelphia, Pa.) using the GCRMA algorithm and Array Assistlite 3.4 program. Visualization of gene profile was done using Spotfire software.

Experimental Example #1

Cell Culture Evaluation of Compound a Molecule in Comparison to Recombinant Human TPO In order to determine if Compound A has the ability to function as a thrombopoietin receptor (TpoR) agonist and stimulate proliferation and differentiation of human megakaryocytes, a number of cell culture experiments were performed using the Tpo dependent cell line (N2C-TPO) as well as normal human CD34+ cells. The ability of Compound A to stimulate proliferation of the TPO dependent cell line N2C-TPO was found to exhibit a dose dependent augmentation of cell proliferation between 1 and 10 uM, with maximal effects at 5-10 µM. Consequently the 5 µM dose was used in further experiments where properties of rhTPO versus Compound A were directly compared.

Normal human progenitor cells (CD34+) were used to evaluate capability of Compound A to stimulate proliferation and differentiation of megakaryocytes. CD34+ cells were plated in fibrin clots and cultured for 10 days, after which time colonies were fixed and stained with antibody specific for megakaryocytic marker CD41. The number of megakaryocyte colonies obtained from cells stimulated with Compound A was slightly lower when compare to the number of megakaryocyte colonies from cells stimulated with rhTPO, however there was no difference in size or shape of the colony (FIG. 1). These results were also confirmed by liquid culture of human progenitor cells. CD34+ cells were incubated in cytokines with rhTPO or Compound A for periods of 7-10 days, after which time cells in culture were examined for degree of polyploidization, and expression of megakaryocyte lineage markers CD41 and CD61. 14% of cells grown in Compound A showed greater than 4N DNA content compared to 8% in rhTPO. These same cells expressed the megakaryocyte markers CD41 and CD61 on 35% of cells, comparable to the results with rhTPO.

Experimental Example #2

Differential Effects of Compound A on Primary Leukemia Cells

Figure 2:
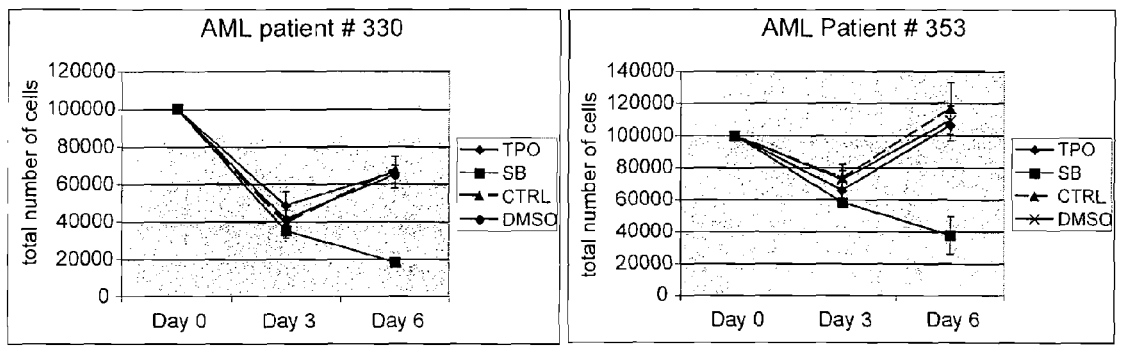
FIG. 2, comprising
Figure 2:
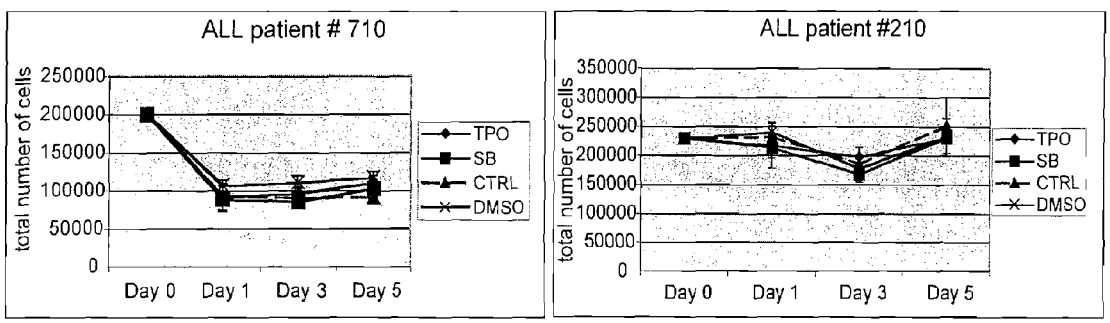
Figure 2:
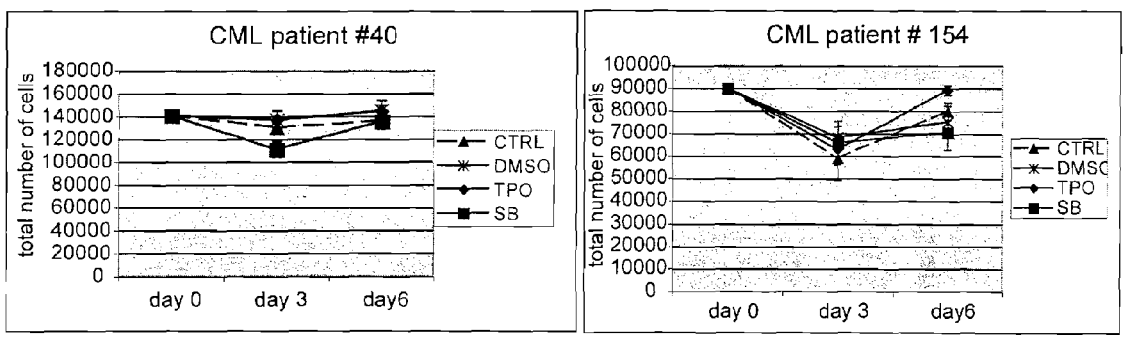

Samples were obtained from 18 patients with acute myelogenous leukemia (AML), 7 patients with acute lymphocytic leukemia (ALL) and 3 patients with chronic myelogenous leukemia (CML). In 17 out of 18 tested AML samples, Compound A inhibited cell proliferation 70-90% when compared to untreated controls or cells cultured with rhTPO (FIG. 2A). No significant effect of Compound A was observed in primary cells from ALL and CML patient samples (FIGS. 2B and C).

Figure 3:
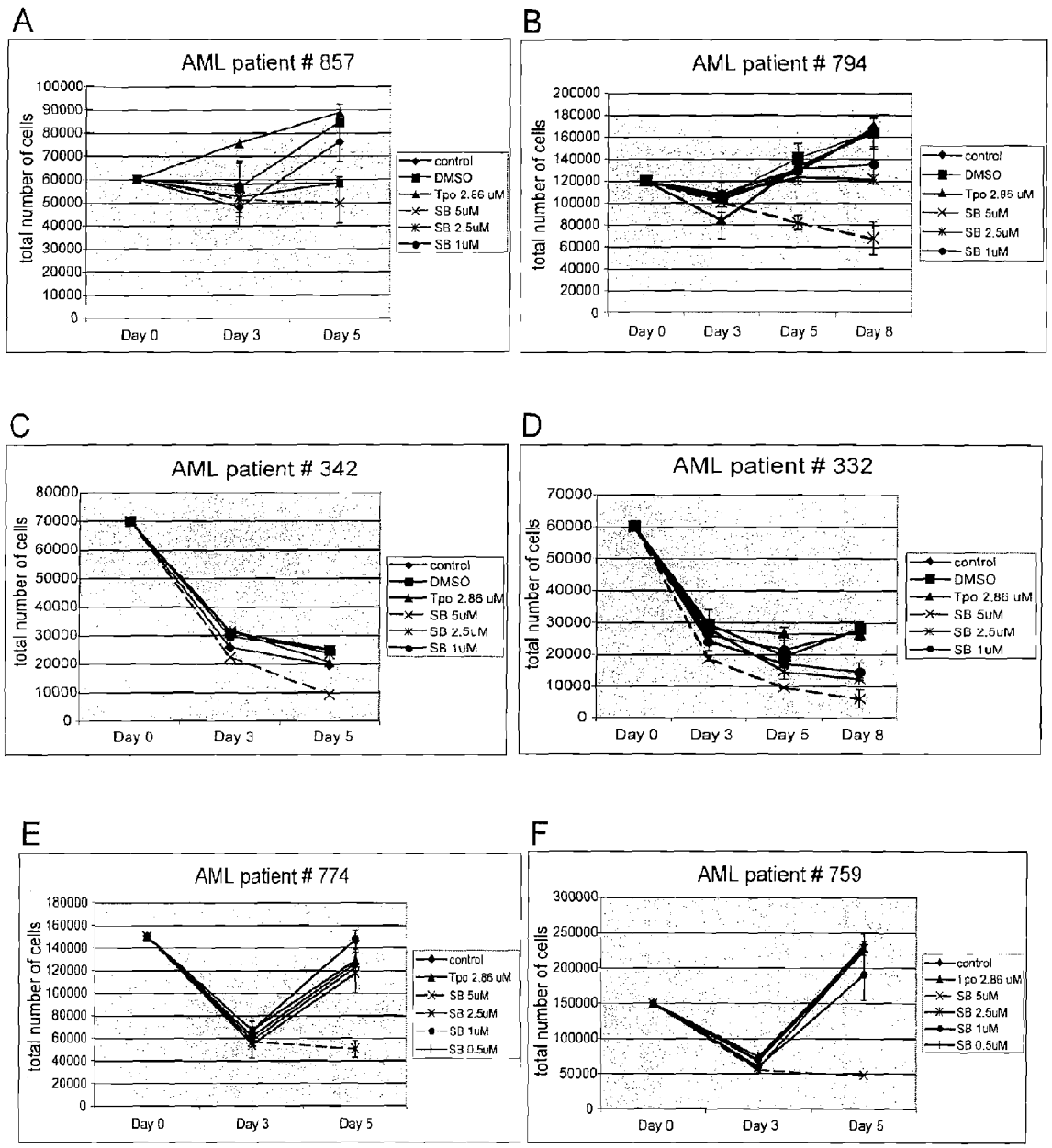
FIG. 3, comprising

Further the effect of various doses of Compound A (1 µM, 2.5 µM and 5 µM) on AML samples was examined. This experiment was performed on 6 different samples. In 3 samples doses of 1 and 2.5 µM Compound A had an effect on cell proliferation. In samples 857 and 332 the inhibition of cell proliferation by 1 and 2.5 µM doses of Compound A was similar to the inhibition achieved with 5 µM dose (FIG. 3). In the remaining 3 samples, doses of 1 µM and 2.5 µM Compound A had no effect on cell proliferation and survival. In these cases, the only 5 µM Compound A inhibited leukemia cell growth and proliferation. No significant effects on cell growth or viability were observed in the ALL or CML patient samples.

Experimental Example #3

Comparison of Signaling Pathways Stimulated by rhTPO and Compound A

To understand the mechanism by which Compound A triggers cell death of AML cells, the intracellular signaling pathways stimulated by rhTPO and Compound A were compared.

These studies were carried out on hematopoietic progenitor cells (CD34+) as well as a megakaryoblastic cell line, N2C-TPO, engineered to express TpoR and wherein cell proliferation is controlled by stimulation by Tpo.

Figure 4:
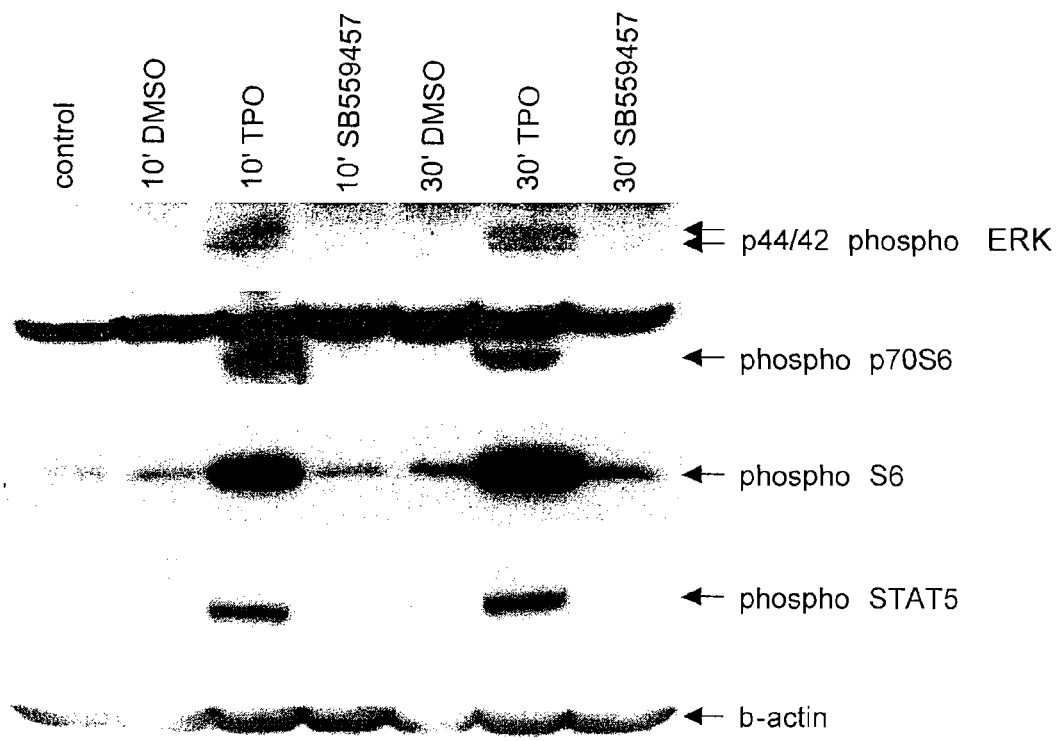
FIG. 4, comprising
Figure 4:
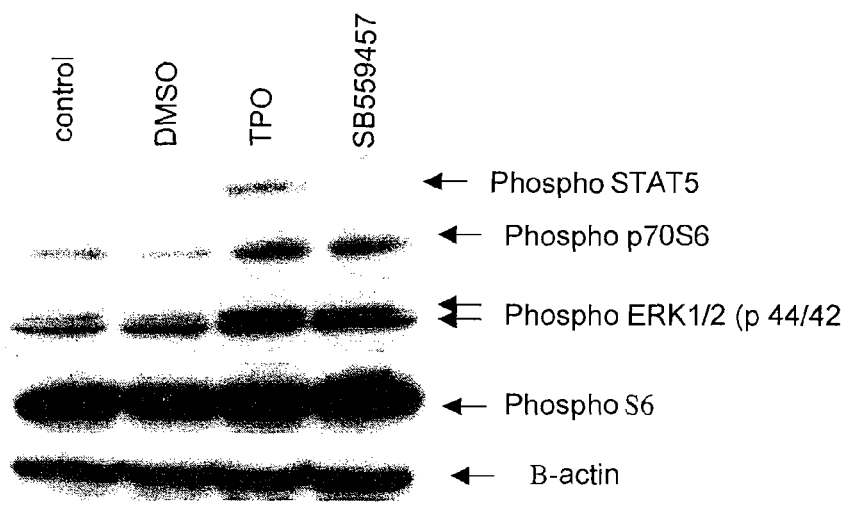

The effect of Compound A on phosphorylation of kinases known to be important in the Tpo signaling pathway was examined. Kinases evaluated include STAT5, ERK, p70S6, and ribosomal kinase S6. N2C-TPO cells stimulated with rhTPO for 10 or 30 minutes showed high phosphorylation level of all the kinases listed above. However, when cells were exposed to Compound A for 10 or 30 minutes, none of those kineses were activated (FIG. 4A). The same experiment was performed on human progenitor cells CD34+, which are stimulated by Compound A to differentiate into the megakaryocytes. In contrast to N2C-TPO cells, CD34+ cells showed activation of ERK, p70S6 and S6 ribosomal protein phosphorylation after being exposed to either rhTPO (2.8 µM) or Compound A (5 µM). However only cells exposed to rhTPO stimulated phosphorylation of STAT5, a kinase, which is over-phosphorylated in AML cells (FIG. 4B).

Experimental Example #4

Can rhTPO Stimulation Block the Effect of Compound A on AML Cells

Figure 5:
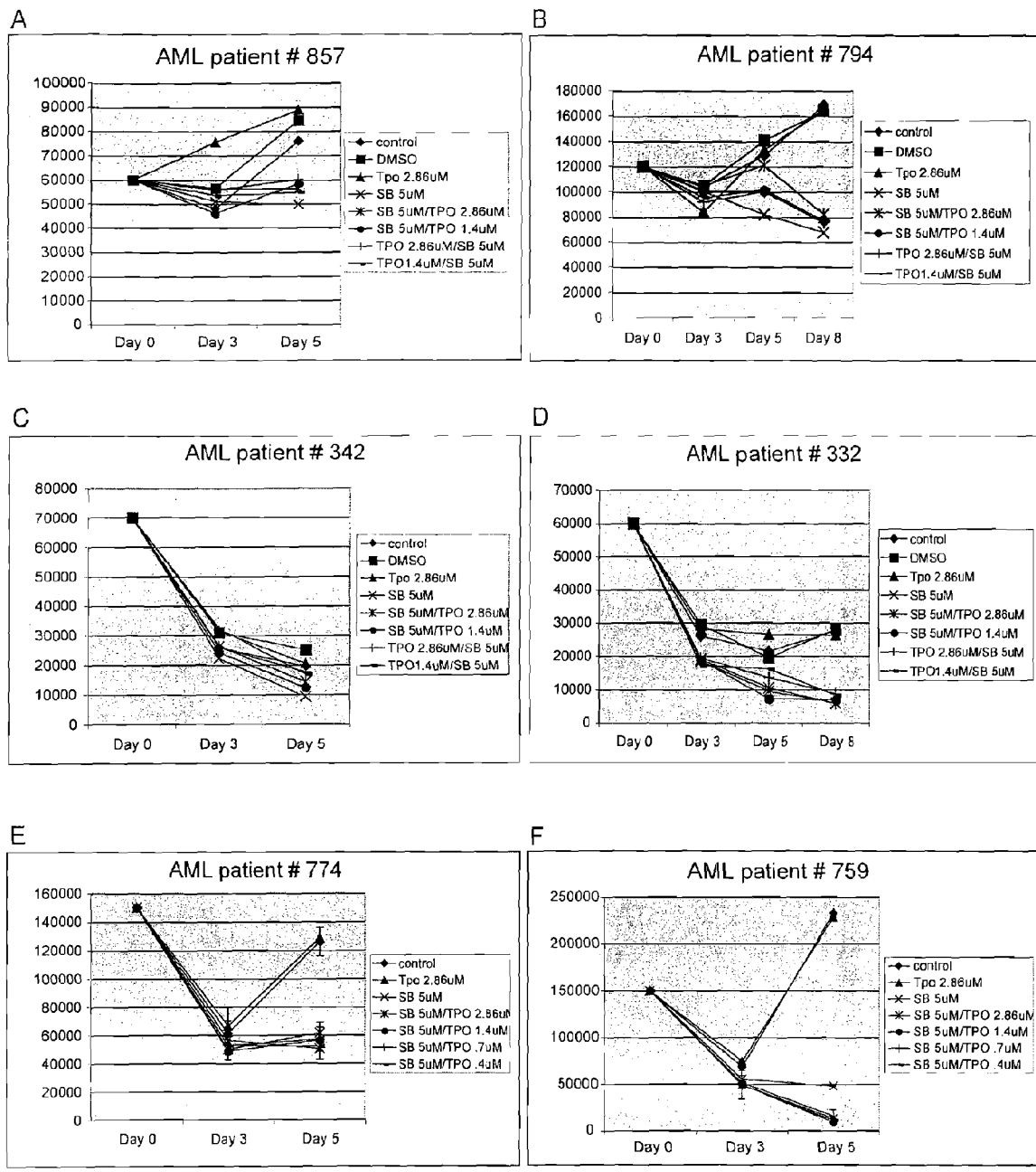
FIG. 5, comprising

Proliferation assays were performed on cells obtained from 6 AML patients. In some experiments, cells were first exposed to Compound A and then stimulated with rhTPO five minutes later. To avoid the possibility of all receptors being occupied by Compound A and therefore preventing rhTPO from binding, other experiments were also performed by first stimulating the cells with rhTPO followed by exposure to Compound A 5 minutes later. In 4 out of 6 samples (857, 774, 759, 342) AML cell survival was not rescued either by adding rhTPO after stimulation with Compound A or by first stimulating cells with rhTPO prior to exposure to Compound A. However, in samples 794 and 332 adding rhTPO did attenuate the Compound A effect (FIG. 5). These results suggest a number of possibilities: first, Compound A may have a much stronger affinity for the TpoR than rhTPO; second, that the $K_D$ rhTPO is much lower and consequently Compound A can displace rhTPO from the receptor; or, third, that Compound A stimulates other pathways that trigger cell death of AML cells.

Figure 6:
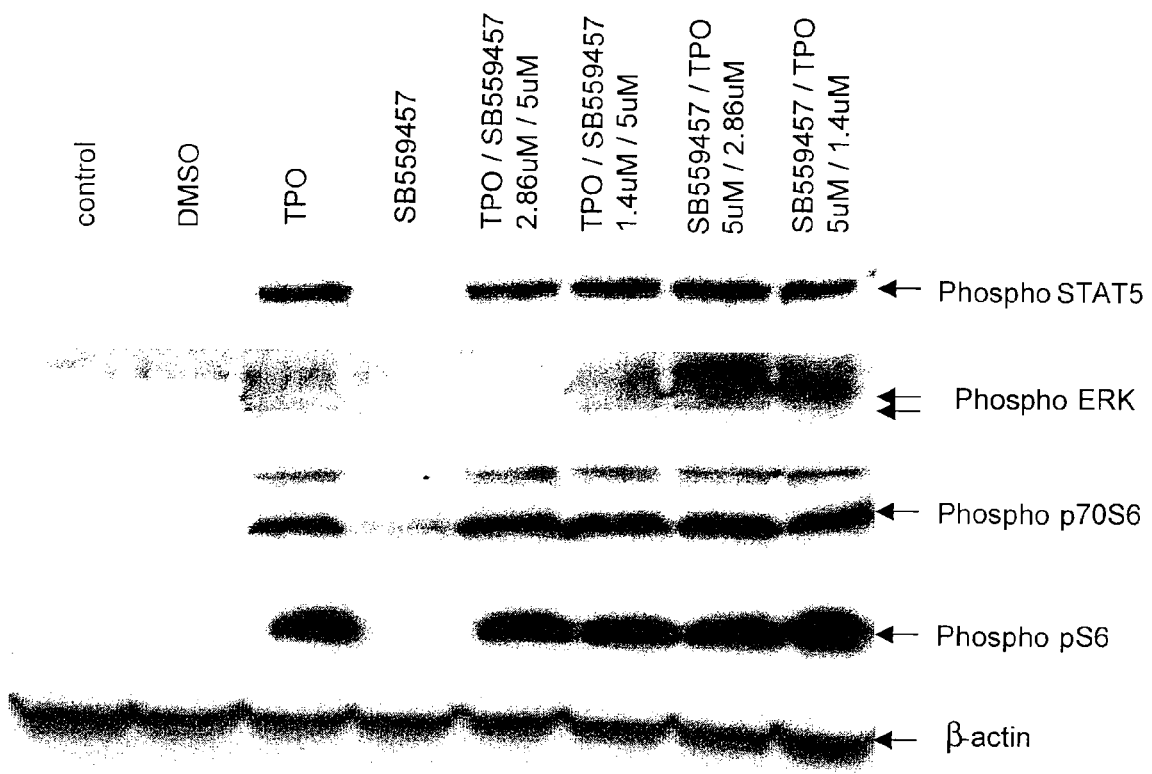
FIG. 6 is an image depicting western blot analysis of ERK1/2, p70S6, S6 and STAT5 kinase phosphorylation in N2C-TPO cells exposed to both Compound A and rhTPO. Compound A is designated as SB.

In an effort to address these possibilities, similar rescue experiments were performed on N2C-TPO cells while evaluating phosphorylation of kinases involved in TPO pathway. In both sets of experiment (either adding rhTPO first and then Compound A, or adding Compound A first and then rhTPO), rescue of phosphorylation of STAT5, ERK p70S6 kinases and S6 ribosomal protein were observed, which were not phosphorylated after stimulation with Compound A alone (FIG. 6). These data suggest that Compound A activates another pathway which leads to death of AML cells.

Experimental Example #5

Microarray Analysis of Differences in Gene Expression in Cells Stimulated with TPO Versus Compound A To further understand the mechanism involved in Compound A signaling, microarray analysis was performed on cells stimulated with Tpo or Compound A using Affymetrix GeneChips. In first set of experiments, the N2C-TPO cell line was probed to establish the optimal time point for further analysis using primary AML cells.

Figure 7:
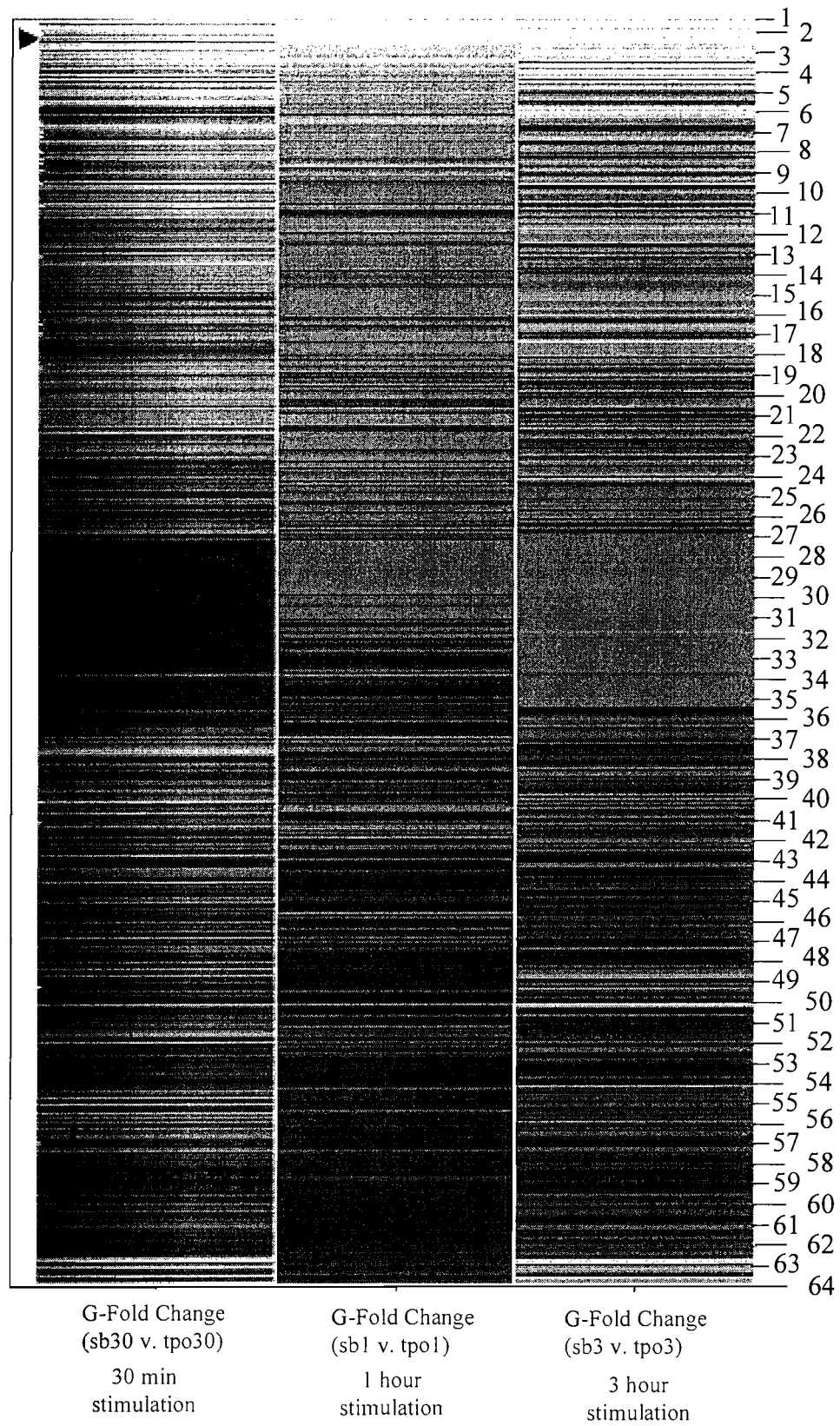
FIG. 7 is an image depicting a heat map illustrating the differences in expression of all tested genes in N2C-TPO cells stimulated with TPO vs Compound A at different time points. Changes in gene expression in cells stimulated with Compound A indicated by a lighter color.

Cells were stimulated with either TPO (2.8 µM) or Compound A (5 µM) for 30 minutes, 1 or 3 hours. RNA was then isolated from cells and used for array experiments. There were significant differences in gene expression after stimulation with Tpo vs Compound A. After 30 minute of stimulation, 200 genes were differentially expressed, after 1 hour of stimulation ~400 genes were differentially expressed and after 3 hours over 2000 genes were either up or down regulated in Compound A samples as copared to samples stimulated by TPO (FIG. 7).

Figure 8A:
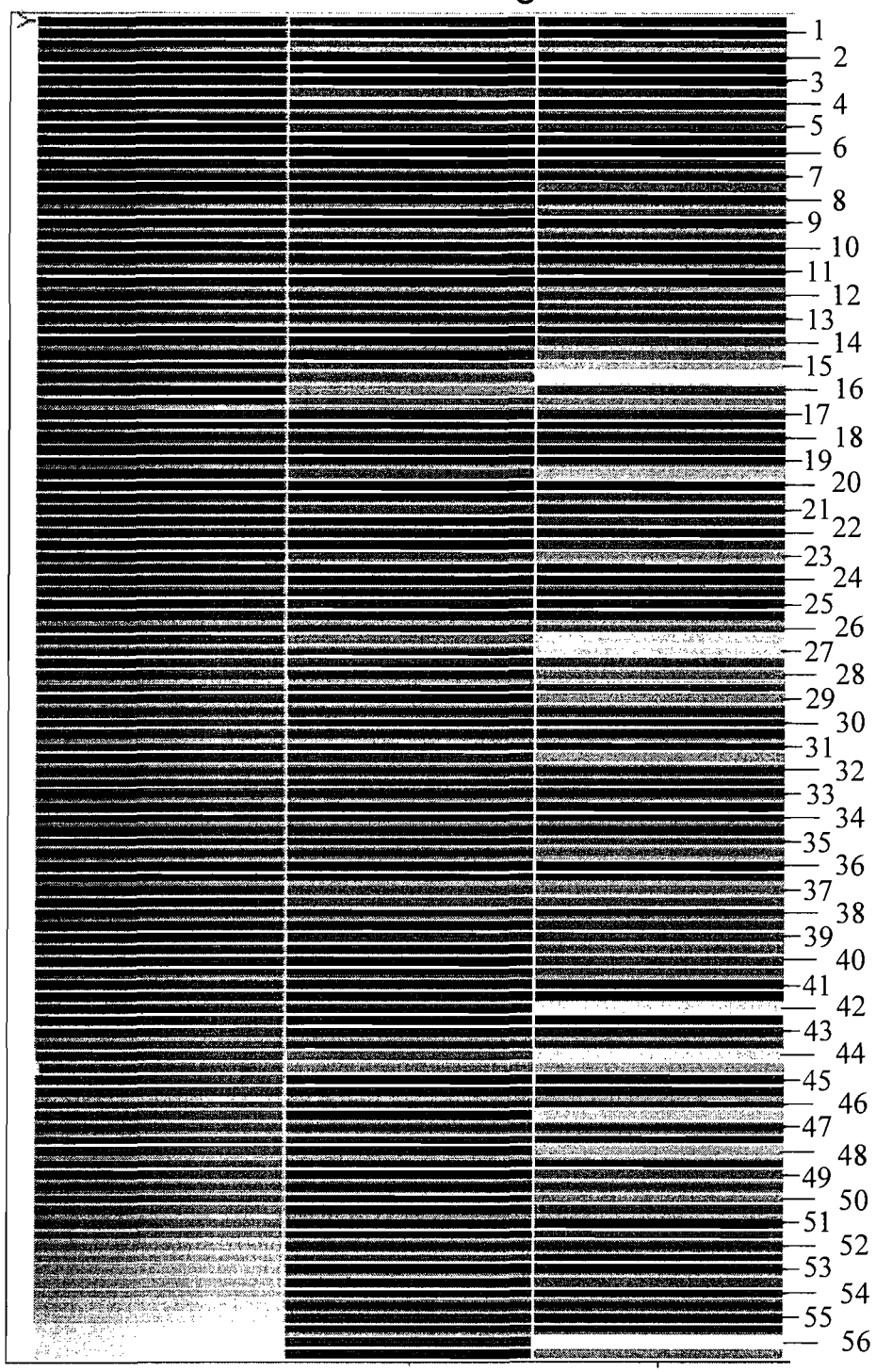
FIG. 8A and FIG. 8B, is a series of images depicting heat maps depicting gene regulation in response to TPO vs. Compound A stimulation.
Figure 8B:
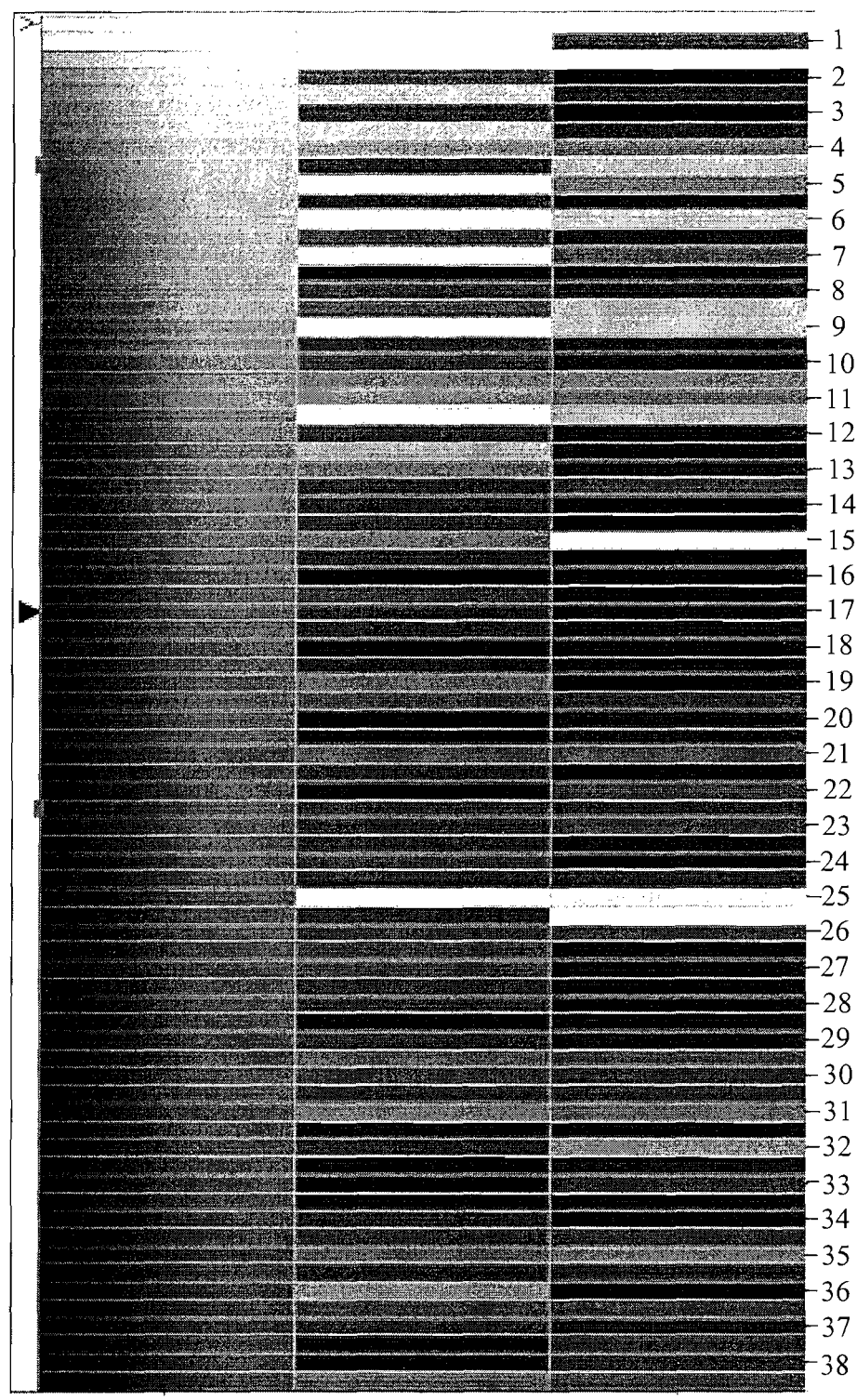
Figure 9A:
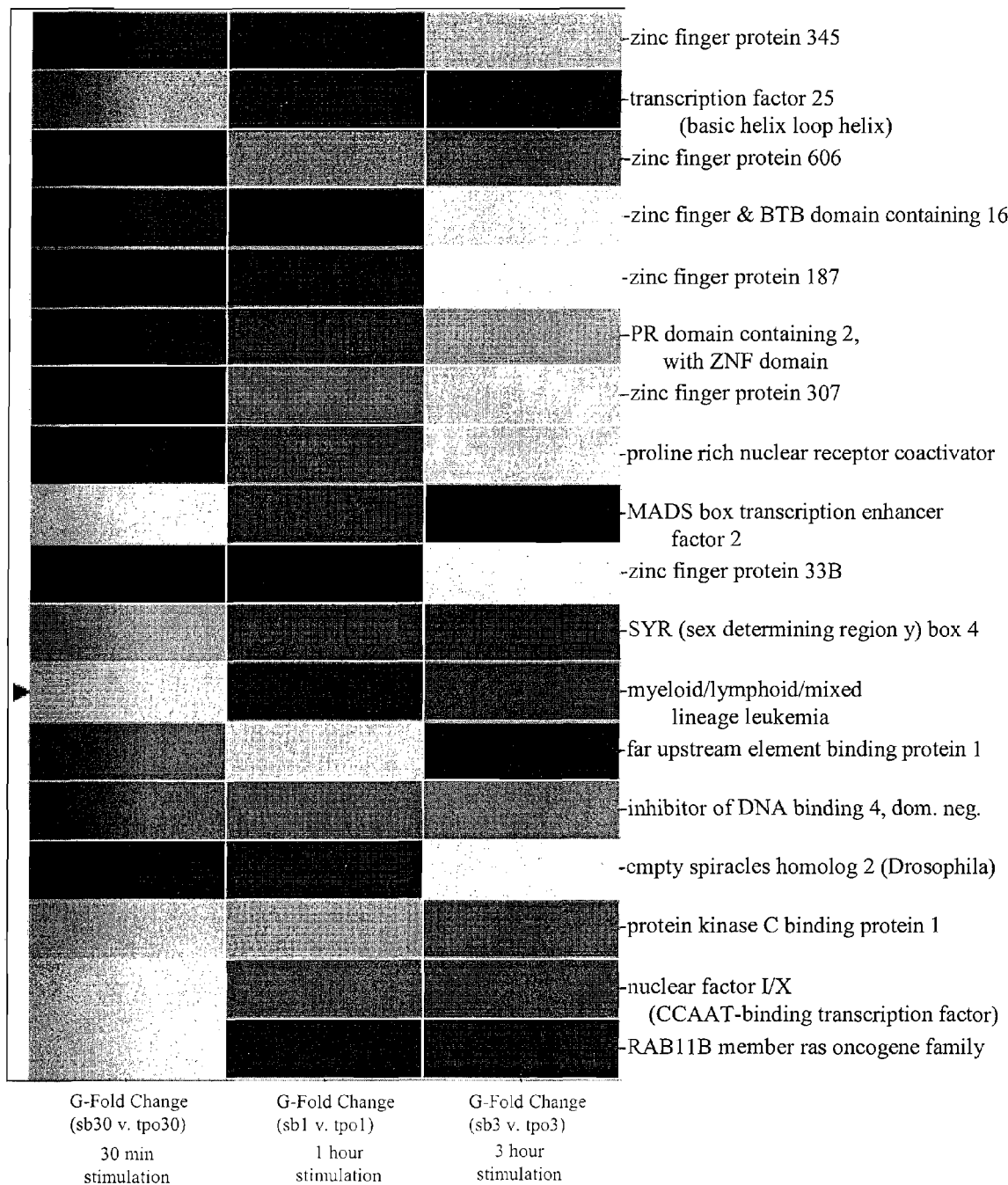
FIG. 9A and FIG. 9B, is a series of images depicting heat maps showing the regulation of transcription factors in N2C-TPO cells stimulated with TPO vs. Compound A.
Figure 9B:
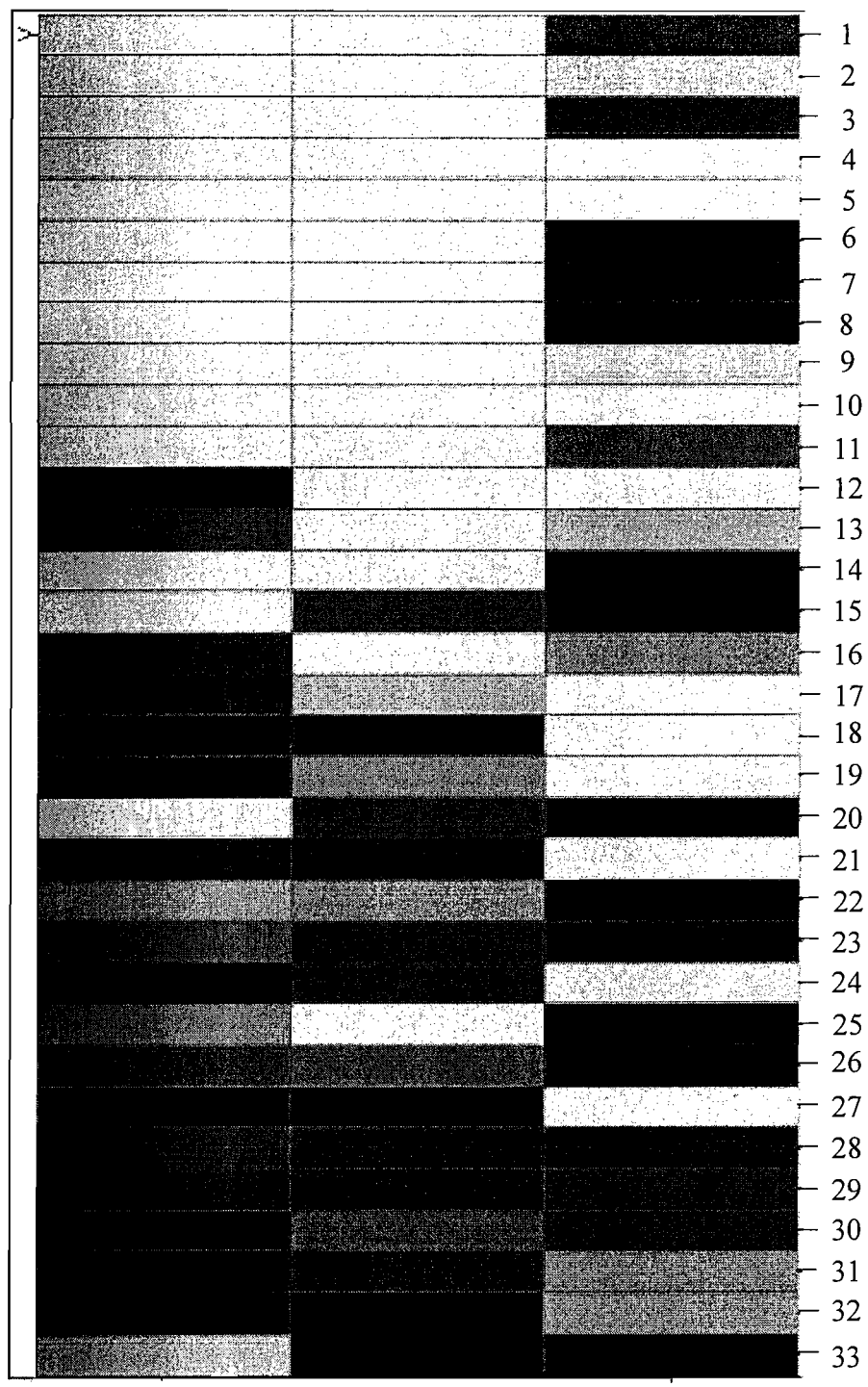

Among of these genes, differences in expression of number of genes involved in apoptotic pathway were observed (FIG. 8) as well as transcription factors (FIG. 9). The most down regulated genes (50-200 times fold change) included the family of early growth factor response genes 1-4 (which encode proteins that act as a nuclear effectors of extracellular signals), a suppressor of cytokine signaling 3, and cytokine inducible SH2-containing protein involved in most cells' signaling pathways.

Experimental Example 6

Apoptosis Assay of Isolated Primary Cells from Human Cancer Patients

Annexin-V is a phospholipid binding protein with a high affinity for phosphatidylserine (PS). Annexin V will not bind normal, intact cells, but necrotic cells are leaky enough to give Annexin V access to inner membrane PS. Propidium iodide stains DNA. The assay therefore identifies cells undergoing apoptosis.

Figure 10:
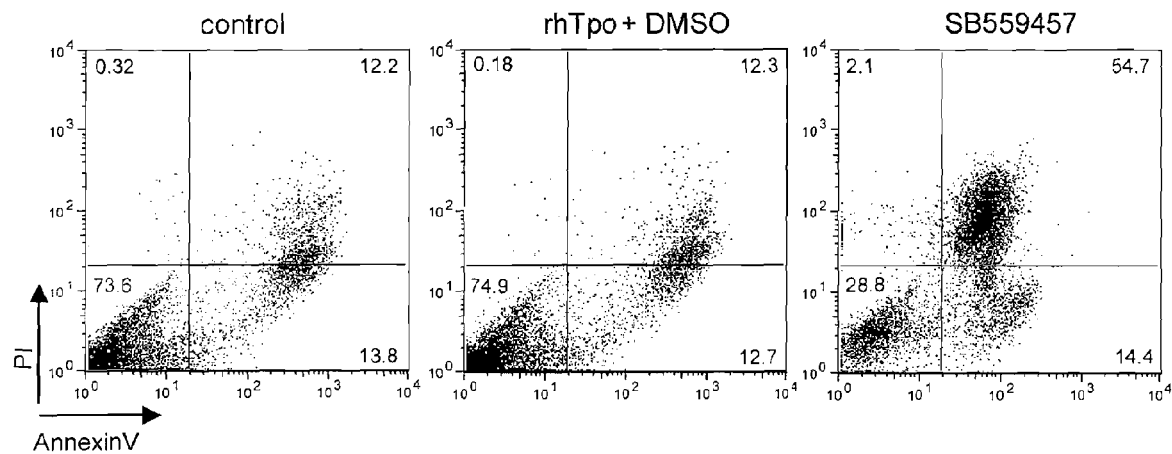
FIG. 10 is a series of images depicting the results of an apoptosis assay performed on primary cells isolated from human patients diagnosed with either AML or ALL. The upper set of three panels depict data obtained from AML patient 774 where isolated primary cells are exposed to control (left panel), rhTpo+DMSO (middle panel) or SB559457 (right panel) then assayed for apoptosis. The bottom set of three panels depict data obtained from ALL patient 710 where primary cells are exposed to control (left panel), rhTpo+DMSO (middle panel) or SB559457 (right panel) then assayed for apoptosis. Axes indicated the number of cells stained for either propidium iodide (PI; y-axis) or annexin V (x-axis).
Figure 10:
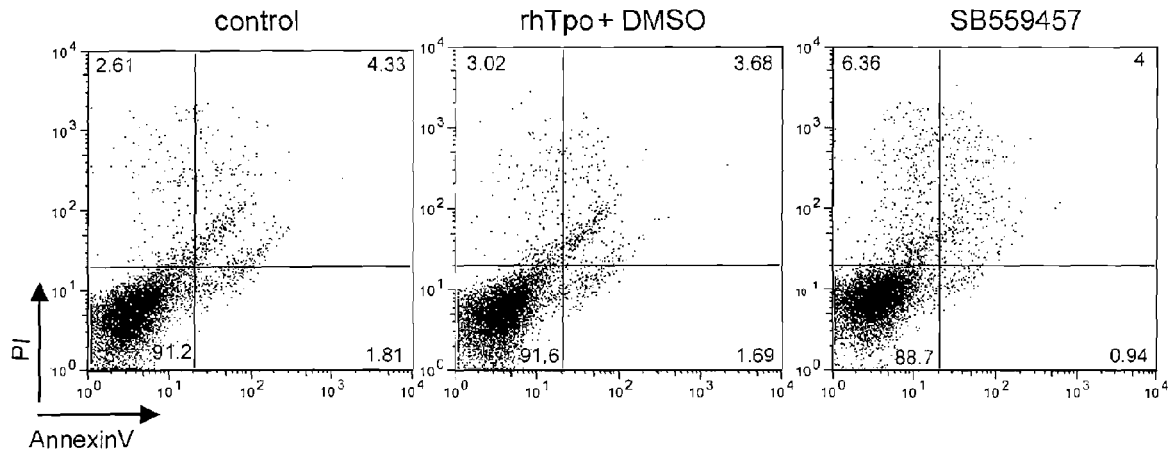

Primary cells were isolated from either an AML (patient 774; top row) or ALL (patient 710; bottom row) patient. The cells were then exposed to either control solution (left pair of panels), rhTpo+DMSO (middle pair of panels), or SB559457 (right pair of panels) for 72 hours. FIG. 10 depicts an increase in Annexin V and PI positive cells in the AML samples exposed to SB55945 for 72 hours (top, right panel) as compared to control cells (top, left panel) and cells stimulated with Tpo+DMSO (top, middle panel). No significant increases in cellular apoptosis could be observed in primary cells isolated from the ALL patient. This suggests that SB559457 induces apoptosis in AML cells.

Experimental Example 7

Molecular Consequences of Differential Signaling in AML Cells

Figure 11:
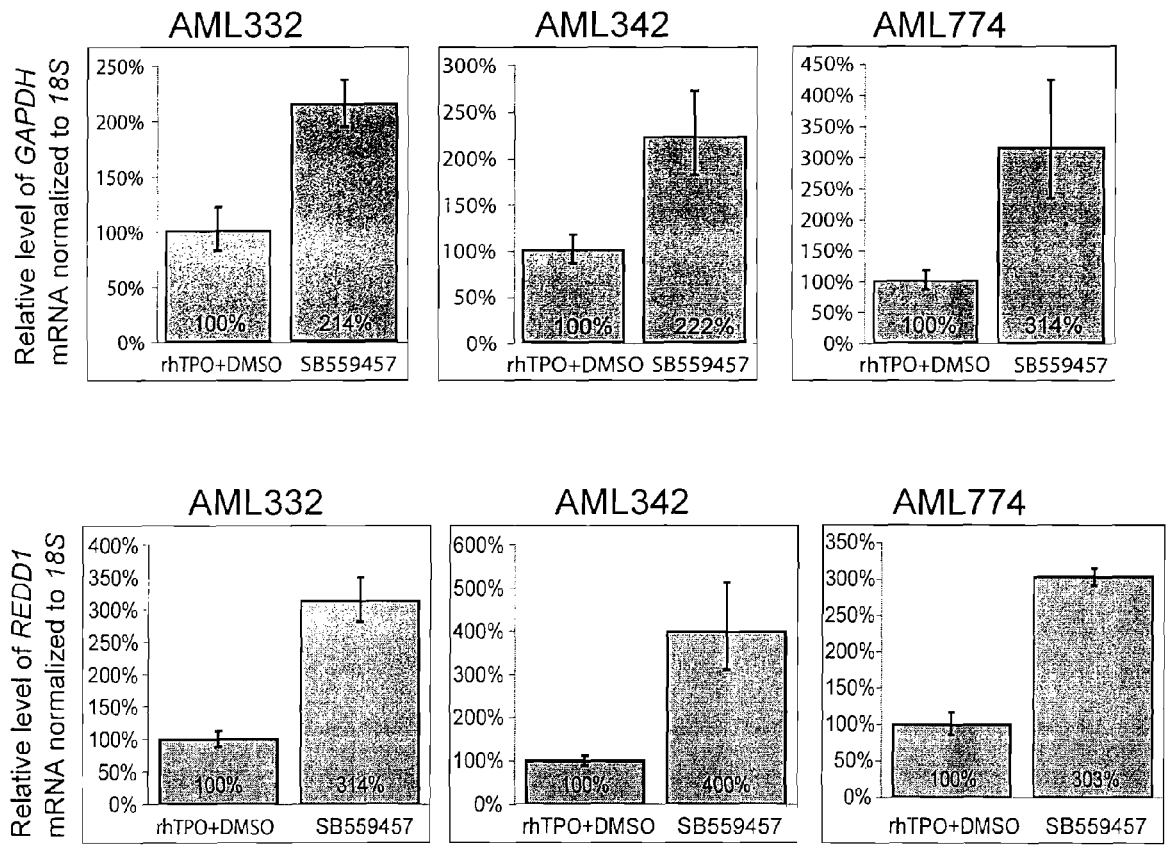
FIG. 11 is a series of graphs depicting a comparison of quantitative RT-PCR analysis of GAPDH (top panel) and Redd1 (bottom panel) mRNA level in primary AML cells stimulated with rhTpo (2.86 µM) or SB559457 (5 µM) for 6 hours.

Affymetrix gene chip analysis was performed on 5 different primary AML cell samples (AML patient 332, 342, 774, and 794). The primary cells were stimulated for 6 hours with either Tpo or SB559457. Statistically significant difference in expression was found in only 2 of 22,000 genes represented on the chips (indicative of a false discovery rate of less than 36%): glyceraldehyde-3-phosphate dehydrogenase (GAPDH) and DNA damage-inducible transcript 4 (also known as Redd1). These results were confirmed using quantitative real time PCR (QRT-PCR). In primary AML samples the expression of GAPDH in cells treated with SB559457 was at least two times higher than in cells treated with rhTpo for the same time (6 hours). Similarly the expression of Redd1 gene was ~3 to 4 times higher in cells incubated with SB559457 than in control cells incubated with rhTpo (FIG. 11).

Figure 12:
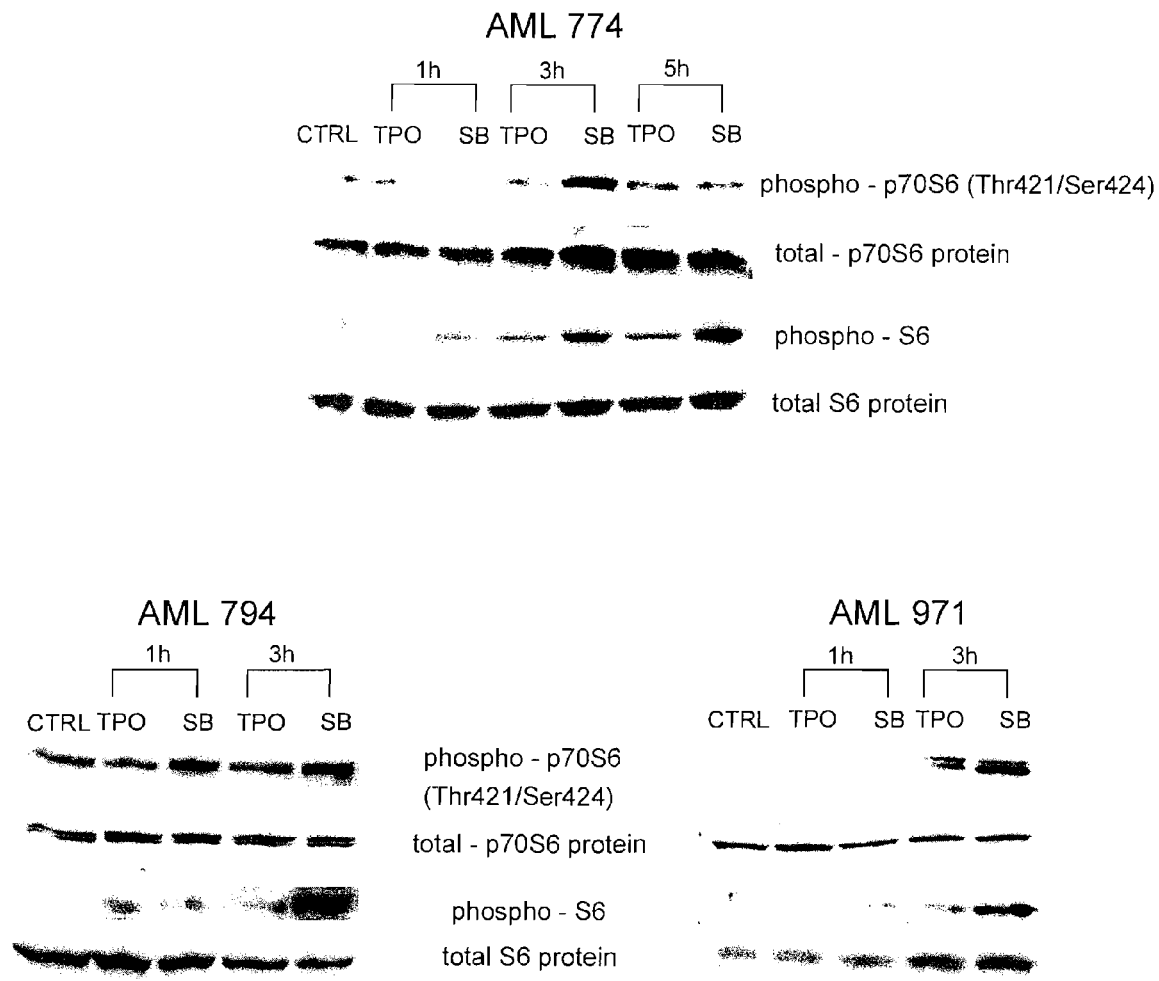
FIG. 12 is a series of images depicting the results of Western blot analysis of p70S and S6 kinase phosphorylation in three different samples of primary AML cells (AML 774, AML 794, and AML 971) after exposure to rhTpo or SB559457 for 1, 3, or 5 hours. Control=unstimulated cells; TPO=cells stimulated with 2.86 6 µM rhTpo+0.05% DMSO; SB=cells stimulated with µM SB559457.

In an effort to establish a correlation between cell signaling and array data, phosphorylation of kinases involved in Tpo signaling pathway in primary leukemia cells was examined. Phosphorylation of ribosomal S6 and p70S6 kinases were compared in cells stimulated with SB559457 (5 µM) and Tpo (2.86 µM) for 1, 3 and 5 hours in 3 primary AML samples. In both AML samples, cells stimulated with SB559457 for 3 hours showed high phosphorylation of p70S6 kinase at Thr421/Ser424 and ribosomal kinase S6, while in unstimulated control cells and cells stimulated with Tpo, none or very little phosphorylation of those kinases was detected (FIG. 12).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating acute myelogenous leukemia in a human 3'-{N'-[1-(3,4-dimethylphenyl)-3-methyl-5-oxo-1,5-dihydropyrazol-4-ylidene]hydrazine}-5'-fluoro-2'-hydroxy-biphenyl-3-carboxylic acid, said method comprising administering a therapeutically effective amount of, to said human.

2. The method of claim 1, where the thrombopoietin receptor agonist is administered to said human as a pharmaceutical composition.

3. The method of claim 2, wherein said pharmaceutical composition is administered orally to said human.

* * * * *